US012559777B2

(12) United States Patent
Green et al.

(10) Patent No.: US 12,559,777 B2
(45) Date of Patent: Feb. 24, 2026

(54) METHODS FOR IMPROVING YIELDS OF L-GLUFOSINATE

(71) Applicant: BASF SE, Ludwigshafen (DE)

(72) Inventors: Brian Michael Green, Lutherville, MD (US); Danielle Marie Estridge, Lutherville, MD (US)

(73) Assignee: BASF SE, Ludwigshafen (DE)

( * ) Notice: Subject to any disclaimer, the term of this patent is extended or adjusted under 35 U.S.C. 154(b) by 483 days.

(21) Appl. No.: 17/272,803

(22) PCT Filed: Sep. 4, 2019

(86) PCT No.: PCT/US2019/049467
§ 371 (c)(1),
(2) Date: Mar. 2, 2021

(87) PCT Pub. No.: WO2020/051188
PCT Pub. Date: Mar. 12, 2020

(65) Prior Publication Data
US 2021/0214754 A1　Jul. 15, 2021

Related U.S. Application Data

(60) Provisional application No. 62/727,322, filed on Sep. 5, 2018.

(51) Int. Cl.
*C12P 7/52* (2006.01)

(52) U.S. Cl.
CPC .............. *C12P 7/52* (2013.01); *C12Y 206/01* (2013.01); *C12Y 401/01071* (2013.01)

(58) Field of Classification Search
None
See application file for complete search history.

(56) References Cited

U.S. PATENT DOCUMENTS

2014/0371417 A1* 12/2014 Pharkya ................... C12N 1/20
564/511
2017/0253897 A1 9/2017 Green et al.

OTHER PUBLICATIONS

Liu, W., et al. 2005 Biochemistry 44(8): 2982-2992. (Year: 2005).*
Lypetska (Fesko) et al., Investigation of one-enzyme systems in the [omega]-transaminase-catalyzed synthesis of chiral amines, J. Mol. Catalysis B: Enzymatic, 96:103-10 (Dec. 2013).
Bartsch et al., Stereospecific production of the herbicide phosphinothricin (glufosinate): purification of aspartate transaminase from *Bacillus stearothermophilus*, cloning of the corresponding gene, aspC, and application in a coupled transaminase process, Appl. Environ. Microbiol., 62(10):3794-9 (1996).
Farnberger et al., In vivo plug-and-play: a modular multi-enzyme single-cell catalyst for the asymmetric amination of ketoacids and ketones, Microb. Cell Fact., 16(1):132 (2017).
International Application No. PCT/US19/049467, International Search Report and Written Opinion, mailed Dec. 3, 2019.

* cited by examiner

*Primary Examiner* — Marsha Tsay
(74) *Attorney, Agent, or Firm* — MARSHALL, GERSTEIN & BORUN LLP

(57) ABSTRACT

Compositions and methods for the production of L-glufosinate are provided. The method involves converting racemic glufosinate to the L-glufosinate enantiomer or converting PPO to L-glufosinate in an efficient manner. In particular, the method involves the specific amination of PPO to L-glufosinate, using L-glutamate, racemic glutamate, or another amine source as an amine donor. PPO can be obtained by the oxidative deamination of D-glufosinate to PRO (2-oxo-4-(hydroxy (methyl) phosphinoyl) butyric acid) or generated via chemical synthesis. PPO is then converted to L-glufosinate using a transaminase in the presence of an amine donor. When the amine donor donates an amine to PPO. L-glufosinate and a reaction by product are formed. Because the PPO remaining represents a yield loss of L-glufosinate, it is desirable to minimize the amount of PPO remaining in the reaction mixture. Degradation, other chemical modification, extraction, sequestration, binding, or other methods to reduce the effective concentration of the by-product. i.e., the corresponding alpha ketoacid or ketone to the chosen amine donor will shift the reaction equilibrium toward L-glufosinate, thereby reducing the amount of PPO and increasing the yield of L-glufosinate. Therefore, the methods described herein involve the conversion or elimination of the alpha ketoacid or ketone by-product to another product to shift the equilibrium towards L-glufosinate.

10 Claims, 4 Drawing Sheets

Specification includes a Sequence Listing.

SEQUENCE LISTING

<160> NUMBER OF SEQ ID NOS: 8

<210> SEQ ID NO 1
<211> LENGTH: 1254
<212> TYPE: PRT
<213> ORGANISM: Mycobacterium smegmatis

<400> SEQUENCE: 1

```
Met Gly Ser Ser His His His His His His Ser Ser Gly Leu Val Pro
1               5                   10                  15

Arg Gly Ser His Met Met Ala Arg Ile Arg Leu Met Ser Ser Ser Pro
            20                  25                  30

Ser Pro Phe Gly Gln Asn Glu Trp Leu Val Glu Glu Met Tyr Arg Lys
        35                  40                  45

Phe Arg Asp Asp Pro Ser Ser Val Asp Pro Ser Trp His Glu Phe Leu
    50                  55                  60

Val Asp Tyr Ser Pro Glu Pro Thr Thr Asp Ser Ala Ser Asn Gly Arg
65                  70                  75                  80

Thr Thr Thr Ala Ala Pro Val Thr Pro Pro Thr Pro Ala Pro Ala Pro
            85                  90                  95

Ala Pro Glu Pro Lys Ala Ala Pro Lys Pro Ala Ala Lys Thr Glu Ala
            100                 105                 110

Lys Pro Ala Lys Pro Ala Lys Ser Ala Thr Pro Ala Lys Gly Asp Glu
        115                 120                 125

Ser Gln Ile Leu Arg Gly Ala Ala Ala Ala Val Val Lys Asn Met Asn
    130                 135                 140

Ala Ser Leu Glu Val Pro Thr Ala Thr Ser Val Arg Ala Ile Pro Ala
145                 150                 155                 160

Lys Leu Met Ile Asp Asn Arg Val Val Ile Asn Asn His Leu Lys Arg
                165                 170                 175

Thr Arg Gly Gly Lys Ile Ser Phe Thr His Leu Leu Gly Tyr Ala Ile
            180                 185                 190

Val Gln Ala Val Lys Lys Phe Pro Asn Met Asn Arg His Phe Ala Val
        195                 200                 205

Val Asp Gly Lys Pro Thr Ala Ile Thr Pro Ala His Thr Asn Leu Gly
        210                 215                 220
```

-continued

```
Leu Ala Ile Asp Leu Gln Gly Lys Asp Gly Asn Arg Ser Leu Val Val
225                 230                 235                 240

Ala Ala Ile Lys Arg Cys Glu Thr Met Arg Phe Gly Gln Phe Ile Ala
                245                 250                 255

Ala Tyr Glu Asp Ile Val Arg Arg Ala Arg Asp Gly Lys Leu Thr Ala
                260                 265                 270

Glu Asp Phe Ser Gly Val Thr Ile Ser Leu Thr Asn Pro Gly Thr Leu
                275                 280                 285

Gly Thr Val His Ser Val Pro Arg Leu Met Gln Gly Gln Gly Ala Ile
                290                 295                 300

Ile Gly Ala Gly Ala Met Glu Tyr Pro Ala Glu Phe Gln Gly Ala Ser
305                 310                 315                 320

Glu Glu Arg Ile Ala Asp Leu Gly Ile Gly Lys Leu Ile Thr Leu Thr
                325                 330                 335

Ser Thr Tyr Asp His Arg Ile Ile Gln Gly Ala Glu Ser Gly Asp Phe
                340                 345                 350

Leu Arg Thr Ile His Gln Leu Leu Leu Asp Asp Asp Phe Phe Asp Glu
                355                 360                 365

Ile Phe Arg Glu Leu Gly Ile Pro Tyr Glu Pro Val Arg Trp Arg Thr
                370                 375                 380

Asp Asn Pro Asp Ser Ile Glu Asp Lys Asn Ala Arg Val Ile Glu Leu
385                 390                 395                 400

Ile Ala Ala Tyr Arg Asn Arg Gly His Leu Met Ala Asp Ile Asp Pro
                405                 410                 415

Leu Arg Leu Asp Asn Thr Arg Phe Arg Ser His Pro Asp Leu Asp Val
                420                 425                 430

Asn Ser His Gly Leu Thr Leu Trp Asp Leu Asp Arg Glu Phe Lys Val
                435                 440                 445

Asp Gly Phe Ala Gly Val Gln Arg Lys Lys Leu Arg Asp Ile Leu Ser
        450                 455                 460

Val Leu Arg Asp Ala Tyr Cys Arg His Val Gly Val Glu Tyr Thr His
465                 470                 475                 480

Ile Leu Glu Pro Glu Gln Gln Arg Trp Ile Gln Glu Arg Val Glu Thr
                485                 490                 495

Lys His Asp Lys Pro Thr Val Ala Glu Gln Lys Tyr Ile Leu Ser Lys
                500                 505                 510

Leu Asn Ala Ala Glu Ala Phe Glu Thr Phe Leu Gln Thr Lys Tyr Val
                515                 520                 525

Gly Gln Lys Arg Phe Ser Leu Glu Gly Ala Glu Thr Val Ile Pro Met
        530                 535                 540

Met Asp Ala Val Ile Asp Gln Cys Ala Glu His Gly Leu Asp Glu Val
545                 550                 555                 560

Val Ile Ala Met Pro His Arg Gly Arg Leu Asn Val Leu Ala Asn Ile
                565                 570                 575

Val Gly Lys Pro Tyr Ser Gln Ile Phe Ser Glu Phe Glu Gly Asn Leu
                580                 585                 590

Asn Pro Ser Gln Ala His Gly Ser Gly Asp Val Lys Tyr His Leu Gly
                595                 600                 605

Ala Thr Gly Thr Tyr Ile Gln Met Phe Gly Asp Asn Asp Ile Glu Val
        610                 615                 620

Ser Leu Thr Ala Asn Pro Ser His Leu Glu Ala Val Asp Pro Val Leu
625                 630                 635                 640
```

-continued

```
Glu Gly Leu Val Arg Ala Lys Gln Asp Leu Leu Asp Thr Gly Glu Glu
            645                 650                 655

Gly Ser Asp Asn Arg Phe Ser Val Val Pro Leu Met Leu His Gly Asp
            660                 665                 670

Ala Ala Phe Ala Gly Gln Gly Val Val Ala Glu Thr Leu Asn Leu Ala
            675                 680                 685

Leu Leu Arg Gly Tyr Arg Thr Gly Gly Thr Ile His Ile Val Val Asn
        690                 695                 700

Asn Gln Ile Gly Phe Thr Thr Ala Pro Thr Asp Ser Arg Ser Ser Glu
705                 710                 715                 720

Tyr Cys Thr Asp Val Ala Lys Met Ile Gly Ala Pro Ile Phe His Val
            725                 730                 735

Asn Gly Asp Asp Pro Glu Ala Cys Ala Trp Val Ala Arg Leu Ala Val
            740                 745                 750

Asp Phe Arg Gln Ala Phe Lys Lys Asp Val Val Ile Asp Met Leu Cys
            755                 760                 765

Tyr Arg Arg Arg Gly His Asn Glu Gly Asp Asp Pro Ser Met Thr Gln
        770                 775                 780

Pro Tyr Met Tyr Asp Val Ile Asp Thr Lys Arg Gly Ser Arg Lys Ala
785                 790                 795                 800

Tyr Thr Glu Ala Leu Ile Gly Arg Gly Asp Ile Ser Met Lys Glu Ala
            805                 810                 815

Glu Asp Ala Leu Arg Asp Tyr Gln Gly Gln Leu Glu Arg Val Phe Asn
            820                 825                 830

Glu Val Arg Glu Leu Glu Lys His Glu Ile Glu Pro Ser Glu Ser Val
            835                 840                 845

Glu Ala Asp Gln Gln Ile Pro Ser Lys Leu Ala Thr Ala Val Asp Lys
        850                 855                 860

Ala Met Leu Gln Arg Ile Gly Asp Ala His Leu Ala Leu Pro Glu Gly
865                 870                 875                 880

Phe Thr Val His Pro Arg Val Arg Pro Val Leu Glu Lys Arg Arg Glu
            885                 890                 895

Met Ala Tyr Glu Gly Arg Ile Asp Trp Ala Phe Ala Glu Leu Leu Ala
            900                 905                 910

Leu Gly Ser Leu Ile Ala Glu Gly Lys Leu Val Arg Leu Ser Gly Gln
        915                 920                 925

Asp Thr Gln Arg Gly Thr Phe Thr Gln Arg His Ala Val Ile Val Asp
    930                 935                 940

Arg Lys Thr Gly Glu Glu Phe Thr Pro Leu Gln Leu Leu Ala Thr Asn
945                 950                 955                 960

Pro Asp Gly Thr Pro Thr Gly Gly Lys Phe Leu Val Tyr Asn Ser Ala
            965                 970                 975

Leu Ser Glu Phe Ala Ala Val Gly Phe Glu Tyr Gly Tyr Ser Val Gly
            980                 985                 990

Asn Pro Asp Ala Met Val Leu Trp  Glu Ala Gln Phe Gly  Asp Phe Val
        995                 1000                 1005

Asn Gly  Ala Gln Ser Ile Ile  Asp Glu Phe Ile Ser  Ser Gly Glu
    1010                 1015                 1020

Ala Lys  Trp Gly Gln Leu Ser  Asp Val Val Leu Leu  Leu Pro His
    1025                 1030                 1035

Gly His  Glu Gly Gln Gly Pro  Asp His Thr Ser Gly  Arg Ile Glu
    1040                 1045                 1050

Arg Phe  Leu Gln Leu Trp Ala  Glu Gly Ser Met Thr  Ile Ala Met
```

```
        1055              1060              1065

Pro Ser  Thr Pro Ala Asn Tyr  Phe His Leu Leu Arg  Arg His Gly
    1070              1075              1080

Lys Asp  Gly Ile Gln Arg Pro  Leu Ile Val Phe Thr  Pro Lys Ser
    1085              1090              1095

Met Leu  Arg Asn Lys Ala Ala  Val Ser Asp Ile Arg  Asp Phe Thr
    1100              1105              1110

Glu Ser  Lys Phe Arg Ser Val  Leu Glu Glu Pro Met  Tyr Thr Asp
    1115              1120              1125

Gly Glu  Gly Asp Arg Asn Lys  Val Thr Arg Leu Leu  Leu Thr Ser
    1130              1135              1140

Gly Lys  Ile Tyr Tyr Glu Leu  Ala Ala Arg Lys Ala  Lys Glu Asn
    1145              1150              1155

Arg Glu  Asp Val Ala Ile Val  Arg Ile Glu Gln Leu  Ala Pro Leu
    1160              1165              1170

Pro Arg  Arg Arg Leu Ala Glu  Thr Leu Asp Arg Tyr  Pro Asn Val
    1175              1180              1185

Lys Glu  Lys Phe Trp Val Gln  Glu Glu Pro Ala Asn  Gln Gly Ala
    1190              1195              1200

Trp Pro  Ser Phe Gly Leu Thr  Leu Pro Glu Ile Leu  Pro Asp His
    1205              1210              1215

Phe Thr  Gly Leu Lys Arg Ile  Ser Arg Arg Ala Met  Ser Ala Pro
    1220              1225              1230

Ser Ser  Gly Ser Ser Lys Val  His Ala Val Glu Gln  Gln Glu Ile
    1235              1240              1245

Leu Asp  Thr Ala Phe Gly
    1250

<210> SEQ ID NO 2
<211> LENGTH: 1064
<212> TYPE: PRT
<213> ORGANISM: Scedosporium apiospermum

<400> SEQUENCE: 2

Met Gly Ser Ser His His His His His His Ser Ser Gly Leu Val Pro
1               5                   10                  15

Arg Gly Ser His Met Met Ala Arg Ile Arg Leu Met Leu Arg Asn Ile
            20                  25                  30

Ala Cys Arg Ala Gly Gly Arg Leu Leu Ser Pro Ser Thr Ser Ser Pro
        35                  40                  45

Ala Trp Arg Ser Val Ser Thr Arg Arg Ala Met Ala Val Ala Ser Gln
    50                  55                  60

Lys Thr Arg Tyr Thr Thr Ser Ala Thr Ser Val Pro Pro Asp Thr Ser
65                  70                  75                  80

Asp Asn Phe Leu Ser Gly Ser Ala Ala Ser Tyr Ile Asp Glu Met Tyr
                85                  90                  95

Met Gln Trp Lys Glu Asp Pro Ser Ser Val His Val Ser Trp Gln Val
            100                 105                 110

Tyr Phe Arg Asn Met Glu Ser Gly Asp Met Pro Ile Ser Gln Ala Phe
        115                 120                 125

Ile Pro Pro Asn Leu Val Pro Ser Ala Thr Gly Gly Val Pro Ser
    130                 135                 140

Leu Thr Pro Gly Gln Gly Met Gly His Ser Glu Asn Ser Asp Leu Met
145                 150                 155                 160
```

```
Lys His Leu Lys Val Gln Leu Leu Cys Arg Ala Tyr Gln Ala Arg Gly
                165                 170                 175

His His Lys Ala Asn Val Asp Pro Leu Gly Ile Arg Asn Ser Ser Lys
            180                 185                 190

Gly Phe Gly Asn Val Arg Pro Arg Glu Leu Thr Leu Glu Phe Tyr Asn
            195                 200                 205

Phe Thr Glu Lys Asp Leu Asp Ala Glu Phe Glu Leu Gly Pro Gly Ile
    210                 215                 220

Leu Pro Arg Phe Lys Thr Pro Glu Arg Gln Lys Met Thr Leu Arg Glu
225                 230                 235                 240

Ile Ile Ser Thr Leu Glu His Ile Tyr Ser Gly Ser Phe Gly Val Glu
                245                 250                 255

Phe Ile His Ile Pro Asn Arg Thr Arg Cys Asp Trp Leu Arg Glu Arg
            260                 265                 270

Leu Glu Val Pro Thr Pro Phe Lys Tyr Ser Ile Asp Glu Lys Arg Arg
            275                 280                 285

Ile Leu Asp Arg Leu Ile Trp Ser Ser Ser Phe Glu Ala Phe Leu Ala
    290                 295                 300

Ser Lys Tyr Pro Asn Asp Lys Arg Phe Gly Leu Glu Gly Cys Glu Thr
305                 310                 315                 320

Leu Val Pro Gly Met Lys Ala Leu Ile Asp Arg Ser Val Asp Tyr Gly
                325                 330                 335

Val Lys Asp Ile Val Ile Gly Met Pro His Arg Gly Arg Leu Asn Val
            340                 345                 350

Leu Ser Asn Val Val Arg Lys Pro Asn Glu Ser Ile Phe Ser Glu Phe
            355                 360                 365

Ala Gly Thr Gln Ser Pro Asp Glu Gly Ser Gly Asp Val Lys Tyr His
    370                 375                 380

Leu Gly Met Asn Phe Glu Arg Pro Thr Pro Ser Gly Lys Arg Val Gln
385                 390                 395                 400

Leu Ser Leu Val Ala Asn Pro Ser His Leu Glu Ala Glu Asp Pro Val
                405                 410                 415

Val Leu Gly Lys Thr Arg Ala Ile Gln His Tyr Asn Asn Asp Glu Ser
            420                 425                 430

Asp His Lys Thr Ala Met Ser Val Leu Leu His Gly Asp Ala Ala Phe
            435                 440                 445

Ala Ala Gln Gly Val Val Tyr Glu Cys Leu Gly Phe His Ser Leu Pro
    450                 455                 460

Ala Phe Ser Thr Gly Gly Thr Ile His Leu Val Val Asn Asn Gln Ile
465                 470                 475                 480

Gly Phe Thr Thr Asp Pro Arg Phe Ala Arg Ser Thr Ala Tyr Cys Thr
                485                 490                 495

Asp Ile Ala Lys Ala Ile Asp Ala Pro Val Phe His Val Asn Ala Asp
            500                 505                 510

Asp Val Glu Ala Val Thr Phe Val Cys Gln Leu Ala Ala Asp Trp Arg
            515                 520                 525

Ala Glu Phe Gln His Asp Val Val Ile Asp Leu Ile Cys Tyr Arg Lys
    530                 535                 540

His Gly His Asn Glu Thr Asp Gln Pro Ser Phe Thr Gln Pro Leu Met
545                 550                 555                 560

Tyr Lys Arg Ile Lys Asp His Glu Pro Gln Ile Asp Ile Tyr Val Asp
                565                 570                 575

Lys Leu Leu Arg Glu Gly Thr Phe Thr Lys Glu Asp Ile Glu Glu His
```

-continued

```
                580                 585                 590

Lys Ser Trp Val Trp Arg Met Leu Gln Asp Ser Phe Asn Arg Ser Lys
        595                 600                 605

Asp Tyr Gln Pro Thr Ser Lys Glu Trp Thr Thr Ser Ala Trp Asn Gly
    610                 615                 620

Phe Lys Ser Pro Lys Glu Leu Ala Thr Glu Ile Leu Pro His Asn Pro
625                 630                 635                 640

Thr Ala Val Asp Glu Gln Thr Leu Lys His Ile Gly Asp Val Ile Gly
                645                 650                 655

Ser Tyr Pro Glu Gly Phe Thr Val His Asn Asn Leu Lys Arg Ile Leu
            660                 665                 670

Lys Asn Arg Ser Lys Ser Val Leu Asp Gly Ala Lys Asn Ile Asp Phe
        675                 680                 685

Pro Thr Ala Glu Ala Leu Ala Phe Gly Ser Leu Val Thr Glu Gly Asn
        690                 695                 700

His Val Arg Val Ser Gly Gln Asp Val Glu Arg Gly Thr Phe Ser Gln
705                 710                 715                 720

Arg His Ala Val Phe His Asp Gln Glu Thr Glu Asp Thr Tyr Thr Pro
                725                 730                 735

Leu Gln His Leu Ser Lys Asp Gln Gly Lys Phe Val Ile Ser Asn Ser
            740                 745                 750

Ser Leu Ser Glu Phe Gly Ala Leu Gly Phe Glu Tyr Gly Tyr Ser Leu
            755                 760                 765

Gln Ser Pro Asn Ala Leu Val Met Trp Glu Ala Gln Phe Gly Asp Phe
        770                 775                 780

Ala Asn Asn Ala Gln Cys Ile Ile Asp Gln Phe Val Ala Ser Gly Glu
785                 790                 795                 800

Val Lys Trp Met Gln Arg Thr Gly Leu Val Met Ser Leu Pro His Gly
                805                 810                 815

Tyr Asp Gly Gln Gly Pro Glu His Ser Ser Gly Arg Leu Glu Arg Tyr
            820                 825                 830

Leu Gln Leu Ser Asn Glu Asp Pro Arg Ile Phe Pro Ser Glu Asp Lys
        835                 840                 845

Leu Ala Arg Gln His Gln Asp Cys Asn Met Gln Ile Val Tyr Met Thr
    850                 855                 860

Glu Pro Ser Asn Leu Phe His Val Leu Arg Arg Gln Met Cys Arg Gln
865                 870                 875                 880

Phe Arg Lys Pro Leu Val Ile Phe Phe Ser Lys Ser Leu Leu Arg His
                885                 890                 895

Pro Leu Ala Arg Ser Ser Leu Asp Glu Phe Thr Gly Asp Ser Ser Phe
            900                 905                 910

Arg Trp Ile Ile Glu Asp Pro Glu His Lys Thr Gly Val Ile Lys Ser
        915                 920                 925

Pro Glu Glu Ile Asp Arg Val Ile Leu Cys Thr Gly Gln Val Tyr Thr
    930                 935                 940

Ala Leu His Lys Tyr Arg Gln Asp His Gln Ile Asp Asn Val Ala Phe
945                 950                 955                 960

Thr Arg Ile Glu Gln Leu Asn Pro Phe Pro Trp Gln Gln Leu Lys Glu
                965                 970                 975

Asn Leu Asp Met Tyr Pro Asn Ala Lys Thr Ile Val Trp Ala Gln Glu
            980                 985                 990

Glu Pro Leu Asn Ala Gly Ala Trp  Ser Phe Thr Gln Pro  Arg Ile Glu
            995                 1000                1005
```

```
Thr Leu Leu Asn His Thr Lys  Tyr His Asp Arg Lys  His Val Met
    1010              1015              1020

Tyr Ala Gly Arg Asn Pro Ser  Ala Ser Val Ala Thr  Gly Met Lys
    1025              1030              1035

His Val His Thr Ala Glu Glu  Ala Glu Leu Leu Glu  Met Ala Phe
    1040              1045              1050

Thr Val Lys Gln Asp Lys Leu  Lys Gly Glu Ala
    1055              1060

<210> SEQ ID NO 3
<211> LENGTH: 1253
<212> TYPE: PRT
<213> ORGANISM: Microbacterium maritypicum

<400> SEQUENCE: 3

Met Gly Ser Ser His His His His His His Ser Ser Gly Leu Val Pro
1               5                   10                  15

Arg Gly Ser His Met Met Ala Arg Ile Arg Leu Met Ser Asn Gln Val
                20                  25                  30

Thr Gly Val Asn Gly Asp Gly Gly Phe Gly Ala Asn Ser Trp Leu Val
            35                  40                  45

Glu Glu Leu Tyr Glu Gln Phe Lys Val Asn Arg Asp Ser Val Asp Lys
    50                  55                  60

Glu Trp Trp Pro Ile Leu Glu Lys Tyr His Ser Glu Thr Ala Ser Ala
65                  70                  75                  80

Ala Pro Ala Ala Thr Pro Asp Ala Pro Ala Ala His Pro Val Thr
                85                  90                  95

Ala Pro Ile Pro Val Ile Gly Ser Gln Pro Val Ala Arg Thr Thr Ala
            100                 105                 110

Lys Pro Ala Ala Ala Ala Pro Ile Pro Ala Gln Ala Pro Lys Pro Ala
            115                 120                 125

Lys Ser Glu Ser Lys Asp Ala Pro Ala Pro Ala Glu Glu Asp Lys Val
    130                 135                 140

Thr Pro Leu Arg Gly Leu Pro Lys Thr Leu Ala Ala Asn Met Asp Glu
145                 150                 155                 160

Ser Leu Thr Val Pro Thr Ala Thr Ser Val Arg Thr Val Pro Ala Lys
                165                 170                 175

Leu Met Ile Asp Asn Arg Ile Val Ile Asn Asn His Met Ala Arg Thr
            180                 185                 190

Arg Gly Gly Lys Val Ser Phe Thr His Leu Ile Gly Trp Ala Leu Ile
            195                 200                 205

Arg Thr Leu Asp Glu Phe Arg Ser Gln Asn Val Phe Tyr Ala Glu Val
    210                 215                 220

Asp Gly Lys Pro Ser Val Val Ala Pro Ala His Val Asn Leu Gly Ile
225                 230                 235                 240

Ala Ile Asp Leu Pro Lys Pro Asp Gly Thr Arg Ala Leu Met Val Pro
                245                 250                 255

Ser Ile Lys Arg Ala Asp Thr Leu Thr Phe Thr Glu Tyr Leu Ser Ala
            260                 265                 270

Tyr Glu Asp Leu Val Thr Arg Ala Arg Gly Asn Lys Leu Thr Ala Gly
            275                 280                 285

Asp Phe Gln Gly Thr Thr Val Ser Leu Thr Asn Pro Gly Gly Ile Gly
    290                 295                 300

Thr Val His Ser Val Pro Arg Leu Met Lys Gly Gln Gly Cys Ile Ile
```

```
305                 310                 315                 320

Gly Ala Gly Ala Leu Glu Tyr Pro Ala Glu Phe Gln Gly Ala Ser Glu
                325                 330                 335

Lys Thr Leu Asn Glu Leu Ala Ile Gly Lys Thr Ile Thr Leu Thr Ser
                340                 345                 350

Thr Tyr Asp His Arg Val Ile Gln Gly Ala Gly Ser Gly Glu Phe Leu
                355                 360                 365

Lys Lys Val His Glu Leu Leu Ile Gly Gln Arg Gly Phe Tyr Asp Asp
                370                 375                 380

Ile Phe Ala Ala Leu Arg Ile Pro Tyr Ala Pro Ile Arg Trp Asn Pro
385                 390                 395                 400

Asp Ile Ala Val Asp Leu Ala Glu Arg Val Asp Lys Gln Ser Arg Val
                405                 410                 415

Gln Glu Leu Ile Asn Ser Phe Arg Val Arg Gly His Leu Met Ala Asp
                420                 425                 430

Ile Asp Pro Leu Glu Tyr Val Gln Arg Ser His Pro Asp Leu Glu Ile
                435                 440                 445

Glu Ser His Gly Leu Thr Phe Trp Asp Leu Asp Arg Glu Phe Val Thr
                450                 455                 460

Gly Gly Phe Gly Gly Arg Arg Ile Ala Lys Leu Arg Asp Ile Leu Gly
465                 470                 475                 480

Val Leu Arg Asp Ser Tyr Cys Arg Thr Leu Gly Ile Glu Tyr Met His
                485                 490                 495

Ile Gln Asp Pro Glu Gln Arg Arg Trp Phe Gln Glu Lys Val Glu Val
                500                 505                 510

Lys Tyr Gln Lys Pro Gly His Asp Glu Gln Leu Arg Val Leu Arg Lys
                515                 520                 525

Leu Asn Glu Ala Glu Ala Phe Glu Thr Phe Leu Gln Thr Lys Phe Val
                530                 535                 540

Gly Gln Lys Arg Phe Ser Leu Glu Gly Gly Glu Ser Leu Ile Pro Leu
545                 550                 555                 560

Leu Asp Glu Ile Leu Gln Gly Ala Ala Thr Ala Gly Leu Glu Gly Ala
                565                 570                 575

Ala Ile Gly Met Ala His Arg Gly Arg Leu Asn Val Leu Thr Asn Ile
                580                 585                 590

Ala Gly Lys Thr Tyr Gly Gln Val Phe Arg Glu Phe Glu Gly Thr Gln
                595                 600                 605

Thr Pro Gly Asn Gln Arg Gly Ser Gly Asp Val Lys Tyr His Leu Gly
                610                 615                 620

Thr Glu Gly Thr Phe Val Ala Asp Asp Asp Ser Glu Leu Pro Val Tyr
625                 630                 635                 640

Leu Ala Ala Asn Pro Ser His Leu Glu Thr Val Asp Gly Val Leu Glu
                645                 650                 655

Gly Ile Val Arg Ala Lys Gln Asp Arg Lys Pro Ile Gly Thr Phe Ala
                660                 665                 670

Trp Leu Pro Ile Leu Val His Gly Asp Ala Ala Phe Ala Gly Gln Gly
                675                 680                 685

Val Val Val Glu Thr Leu Gln Met Ser Gln Leu Arg Gly Tyr Arg Thr
                690                 695                 700

Gly Gly Thr Ile His Val Val Val Asn Asn Gln Val Gly Phe Thr Thr
705                 710                 715                 720

Thr Pro Asn Asp Gly Arg Thr Ser Ile Tyr Ser Thr Asp Val Ala Lys
                725                 730                 735
```

-continued

```
Thr Ile Gln Ala Pro Val Phe His Val Asn Gly Asp Asp Pro Glu Ala
            740                 745                 750

Val Ile His Val Ala Gln Leu Ala Phe Glu Tyr Arg Glu Arg Phe His
            755                 760                 765

Arg Asp Val Val Ile Asp Leu Val Cys Tyr Arg Arg Arg Gly His Asn
    770                 775                 780

Glu Gly Asp Asp Pro Ser Met Thr Gln Pro Leu Met Thr Asp Leu Ile
785                 790                 795                 800

Gln Ala Lys Arg Ser Val Arg Arg Leu Tyr Thr Glu Ser Leu Val Gly
                805                 810                 815

Arg Gly Asp Ile Thr Glu Gln Glu Tyr Asp Glu Ala Lys Ala Asp Phe
                820                 825                 830

Gln Asn Arg Leu Glu Ile Ala Phe Ala Glu Thr His Ala Ala Glu Thr
            835                 840                 845

Gly Ala Leu Pro Ile Ala Pro Glu Gln Ala Pro Val Asp Asp Gln Val
    850                 855                 860

Gly Ala Pro Glu Ile Thr Gly Val Pro Ser Glu Val Ile Gln Met Ile
865                 870                 875                 880

Gly Asp Ala Phe Val Asn Lys Pro Glu Gly Phe Thr Val His Pro Lys
                885                 890                 895

Ile Gln Gln Leu Leu Asp Lys Arg Leu Asp Met Ser Arg Asn Gly Asn
            900                 905                 910

Ile Asp Trp Gly Phe Gly Glu Leu Leu Ala Phe Gly Ser Leu Leu Val
            915                 920                 925

Glu Gly Thr Pro Val Arg Leu Ala Gly Gln Asp Ala Arg Arg Gly Thr
    930                 935                 940

Phe Val Gln Arg His Ala Thr Leu His Asp Arg Ala Asn Gly Gln Glu
945                 950                 955                 960

Trp Leu Pro Leu Ser Asn Leu Ser Asp Ala Gln Gly Arg Phe Phe Val
                965                 970                 975

Tyr Asp Ser Leu Leu Ser Glu Tyr Ala Ala Leu Gly Phe Glu Tyr Gly
            980                 985                 990

Tyr Ser Val Glu Ala Pro Glu Ala  Leu Val Leu Trp Glu  Ala Gln Phe
            995                 1000                1005

Gly Asp  Phe Val Asn Gly Ala  Gln Ser Val Ile Asp  Glu Tyr Ile
    1010                1015                1020

Ser Ala  Ala Glu Gln Lys Trp  Gly Gln Gln Ser Ser  Val Thr Leu
    1025                1030                1035

Leu Leu  Pro His Gly Tyr Glu  Gly Gln Gly Pro Asp  His Ser Ser
    1040                1045                1050

Ala Arg  Ile Glu Arg Phe Leu  Gln Met Cys Ala Gln  Asp Asn Met
    1055                1060                1065

Ile Val  Ser Arg Pro Ser Thr  Pro Ala Ser Tyr Phe  His Leu Leu
    1070                1075                1080

Arg Arg  Gln Ala Tyr Ala Arg  Pro Arg Lys Pro Leu  Ile Val Phe
    1085                1090                1095

Thr Pro  Lys Ala Met Leu Arg  Leu Arg Gly Ala Thr  Ser Pro Val
    1100                1105                1110

Glu Ala  Phe Thr Gln Gly Arg  Phe Glu Pro Val Ile  Asp Asp Asp
    1115                1120                1125

Arg Gly  Leu Asp Arg Thr Ala  Val Lys Arg Val Leu  Val His Ser
    1130                1135                1140
```

```
Gly Lys Val His Trp Asp Leu Arg Ala Glu Leu Glu Lys Asn Pro
    1145                1150                1155

Asn Pro Glu Val Ala Leu Val Arg Leu Glu Gln Leu Tyr Pro Thr
    1160                1165                1170

Pro Ile Asp Glu Leu Lys Ala Ile Thr Asp Ser Tyr Pro Asn Ala
    1175                1180                1185

Glu Leu Val Trp Val Gln Glu Glu Pro Glu Asn Gln Gly Ala Trp
    1190                1195                1200

Pro Phe Leu Ala Leu Ala Phe Ala Asp Val Pro Gly Asp Arg Ser
    1205                1210                1215

Phe Arg Pro Val Ser Arg Pro Ala Ser Ala Ser Pro Ala Thr Gly
    1220                1225                1230

Ser Ser Lys Val His Ala Ala Glu Gln Ala Ala Leu Ile Arg Ala
    1235                1240                1245

Ala Val Thr Leu Gly
    1250

<210> SEQ ID NO 4
<211> LENGTH: 1296
<212> TYPE: PRT
<213> ORGANISM: Arthrobacter enclensis

<400> SEQUENCE: 4

Met Gly Ser Ser His His His His His His Ser Ser Gly Leu Val Pro
1                   5                   10                  15

Arg Gly Ser His Met Met Ala Arg Ile Arg Leu Met Pro Glu Gln Pro
                20              25              30

Ser His Arg Leu Pro Glu Glu Phe Gly Gly Asn Glu Trp Leu Val Asp
        35              40              45

Glu Leu Tyr Glu Gln Tyr Gln Gln Asp Lys Asn Ala Val Asp Ala Lys
    50              55              60

Trp Trp Pro Leu Phe Glu Ser Phe Asp Ser Gly Ser Ser Ser Ser Ser
65              70              75              80

Asn Gly His Ser Ala Gly Ala Ala Ala Asn Pro Pro Thr Thr Lys Leu
            85              90              95

Pro Val Val Asn Ala Ala Pro Ala Ala Pro Ala Pro Ser Pro Ser Ala
            100             105             110

Ala Pro Pro Ala Pro Ala Ala Pro Pro Ala Ala Ala Ala Pro Ala Ala
        115             120             125

Pro Ala Pro Val Lys Lys Ala Pro Ala Thr Glu Ala Arg Asp Gly Gly
        130             135             140

Thr Lys Ser Ser Thr Gly Ser Gly Ala Gln Pro Ile Pro Ala Gln Leu
145             150             155             160

Pro Lys Asn Val Lys Ala Pro Thr Ala Pro Glu Glu Asp Val Val Ser
            165             170             175

Val Leu Arg Gly Pro Ala Lys Ala Ile Ala Thr Asn Met Val Thr Ser
            180             185             190

Leu Glu Val Pro Thr Ala Thr Ser Val Arg Ala Ile Pro Ala Lys Leu
        195             200             205

Leu Ile Asp Asn Arg Val Val Ile Asn Ser Asn Leu Ala Arg Ala Arg
        210             215             220

Gly Gly Lys Val Ser Phe Thr His Leu Ile Gly Tyr Ala Val Ile Arg
225             230             235             240

Ala Leu Ser Gln Phe Pro Ser Met Asn Val Tyr Tyr Asp Glu Val Asp
            245             250             255
```

-continued

```
Gly Lys Pro Val Ala Val Gln Pro Ala His Val Asn Phe Gly Ile Ala
            260                 265                 270

Ile Asp Met Pro Lys Pro Asp Gly Thr Arg Leu Leu Met Val Pro Asn
            275                 280                 285

Ile Lys Lys Ala Glu Thr Leu Asn Phe Ala Glu Phe Trp His Thr Tyr
            290                 295                 300

Glu Asp Leu Ile Lys Arg Ala Arg Asn Gly Lys Leu Thr Ala Glu Asp
305                 310                 315                 320

His Gln Gly Thr Thr Val Ser Leu Thr Asn Pro Gly Gly Ile Gly Thr
                325                 330                 335

Val His Ser Val Pro Arg Leu Ser Lys Gly Gln Ala Ala Ile Ile Gly
                340                 345                 350

Val Gly Ala Leu Asp Tyr Pro Ala Glu Phe Gln Gly Ala Ser Glu Lys
                355                 360                 365

Ile Ile Ala Gln Asn Ala Ile Ser Lys Val Leu Thr Leu Thr Ser Thr
            370                 375                 380

Tyr Asp His Arg Val Ile Gln Gly Ala Gly Ser Gly Glu Phe Leu Lys
385                 390                 395                 400

Leu Val His Gln Leu Leu Leu Gly Ala Gln Asn Phe Tyr Asp Glu Ile
                405                 410                 415

Phe Glu Ala Leu Arg Ile Pro Tyr Glu Pro Val Arg Trp Ser Pro Asp
                420                 425                 430

Leu Gln Val Asp Pro Ala Asp Glu Ile Asn Lys Val Ala Arg Ile Gln
                435                 440                 445

Gln Leu Ile His Ser Phe Arg Val Arg Gly His Leu Met Ala Asp Thr
            450                 455                 460

Asp Pro Leu Glu Tyr Val Gln Arg Lys His Pro Asp Leu Asp Val Leu
465                 470                 475                 480

Thr Tyr Gly Leu Thr Leu Trp Asp Leu Asp Arg Glu Trp Pro Thr Gly
                485                 490                 495

Gly Phe Gly Gly Lys Pro Met Leu Lys Phe Arg Asp Ile Leu Gly Val
                500                 505                 510

Leu Arg Asp Ala Tyr Cys Arg Thr Thr Gly Ile Glu Tyr Met His Ile
            515                 520                 525

Gln Glu Pro Ala Glu Arg Lys Trp Phe Gln Asp Gln Leu Glu His Pro
            530                 535                 540

Tyr Ser Lys Pro Ser Arg Glu Glu Gln Leu Arg Ile Val Ser Arg Leu
545                 550                 555                 560

Asn Ala Ala Glu Ala Phe Glu Thr Phe Leu Gln Thr Lys Phe Val Gly
                565                 570                 575

Gln Lys Arg Phe Ser Leu Glu Gly Gly Glu Ser Leu Ile Pro Leu Leu
                580                 585                 590

Asp Ala Val Ile Ser Glu Ala Ala Asp Asp Gly Leu Asp Glu Val Ala
                595                 600                 605

Ile Gly Met Ala His Arg Gly Arg Leu Asn Val Leu Thr Asn Ile Ala
            610                 615                 620

Gly Lys Thr Tyr Ala Gln Val Phe Arg Glu Phe Glu Gly Thr Gln Asp
625                 630                 635                 640

Pro Arg Ser Val Gln Gly Ser Gly Asp Val Lys Tyr His Leu Gly Thr
                645                 650                 655

Glu Gly Thr Phe Thr Ser Glu Asn Gly Asn Glu Thr Lys Val Tyr Leu
                660                 665                 670
```

-continued

```
Ala Ala Asn Pro Ser His Leu Glu Ala Val Asp Ser Val Leu Glu Gly
        675             680             685

Ile Val Arg Ala Lys Gln Asp Arg Leu Asp Gln Gly Glu Ala Phe Pro
        690             695             700

Val Leu Pro Ile Met Val His Gly Asp Ala Ala Phe Ala Gly Gln Gly
705             710             715             720

Val Val Ala Glu Thr Leu Asn Leu Ser Gln Leu Arg Gly Tyr Arg Thr
            725             730             735

Gly Gly Thr Ile His Val Val Val Asn Asn Gln Val Gly Phe Thr Thr
            740             745             750

Ala Pro Ser Ser Ser Arg Ser Ser Thr Tyr Ser Thr Asp Val Ala Lys
        755             760             765

Met Ile Gln Ala Pro Val Phe His Val Asn Gly Asp Asp Pro Glu Ala
        770             775             780

Val Val Arg Val Gly Gln Leu Ala Tyr Glu Phe Arg Gln Arg Phe His
785             790             795             800

Lys Asp Val Val Ile Asp Met Val Cys Tyr Arg Arg Arg Gly His Asn
            805             810             815

Glu Gly Asp Asp Pro Ser Met Thr Gln Pro Met Met Tyr Asn Leu Ile
            820             825             830

Glu Ala Lys Arg Ser Val Arg Lys Leu Tyr Thr Glu Ala Leu Ile Gly
            835             840             845

Arg Gly Asp Ile Thr Glu Glu Glu Ala Glu Gln Leu Leu Arg Asp Tyr
        850             855             860

Gln Glu Arg Leu Glu Arg Val Phe Ala Glu Thr His Ala Ala Gln Thr
865             870             875             880

Ser Pro Ile Pro Ile Val Thr Ala Asp Ser Ala Ala Val Ser Asp Ile
            885             890             895

Glu Arg Pro Thr Ala Gln Gln Ala Asp Ala Gly Ile Asn Ala Pro Ala
        900             905             910

Ser Thr Ala Ile Ser Ala Asp Thr Leu Ala Arg Ile Gly His Ala His
        915             920             925

Val Glu Ile Pro Glu Gly Phe Thr Val His Ala Lys Leu Lys Gln Leu
        930             935             940

Leu Glu Lys Arg Glu Gln Met Ser Arg Glu Gly Gly Ile Asp Trp Gly
945             950             955             960

Phe Gly Glu Ile Ala Ala Phe Gly Ser Leu Ile Met Glu Gly Val Pro
            965             970             975

Val Arg Leu Ala Gly Gln Asp Ser Arg Arg Gly Thr Phe Val Gln Arg
        980             985             990

His Ala Val Phe His Asp Arg Ala  Asn Gly Asn Glu Trp  Leu Pro Leu
        995             1000            1005

Gly Asn  Leu Ser Glu Gly Gln  Ala Lys Leu Trp Ile  Tyr Asp Ser
    1010            1015            1020

Leu Leu  Ser Glu Tyr Ala Ala  Met Gly Phe Glu Tyr  Gly Tyr Ser
    1025            1030            1035

Val Glu  Arg Pro Asp Ala Leu  Val Leu Trp Glu Ala  Gln Phe Gly
    1040            1045            1050

Asp Phe  Val Asn Gly Ala Gln  Thr Ile Ile Asp Glu  Phe Ile Ser
    1055            1060            1065

Ser Ala  Glu Gln Lys Trp Gly  Gln Arg Ser Ser Leu  Val Leu Met
    1070            1075            1080

Leu Pro  His Gly Tyr Glu Gly  Gln Gly Pro Asp His  Ser Ser Ala
```

-continued

```
            1085                1090                1095

Arg Ile  Glu Arg Phe Leu Gln  Leu Cys Ala Glu Gln  Asn Met Ile
    1100                1105                1110

Val Ala  Asn Pro Thr Thr Ala  Ala Ser His Phe His  Leu Leu Arg
    1115                1120                1125

Arg Gln  Ala Tyr Ser Arg Pro  Arg Lys Pro Leu Ile  Ile Phe Thr
    1130                1135                1140

Pro Lys  Gln Leu Leu Arg Leu  Lys Ala Ala Ala Ser  Ala Val Glu
    1145                1150                1155

Asp Phe  Thr Ser Gly Thr Phe  Arg Pro Val Ile Gly  Glu His Glu
    1160                1165                1170

Gln Leu  Asp Ala Asn Ala Val  Glu Arg Val Leu Leu  Val Ser Gly
    1175                1180                1185

Arg Leu  Tyr Tyr Asp Leu Leu  Ser Thr Arg Gln Lys  Thr Gly Asp
    1190                1195                1200

Lys Thr  Thr Ala Ile Ile Arg  Val Glu Gln Leu Tyr  Pro Leu Pro
    1205                1210                1215

His Glu  Glu Ile Ala Ala Glu  Leu Ala Lys Tyr Pro  Asn Ala Glu
    1220                1225                1230

Val Val  Trp Ala Gln Asp Glu  Pro Ala Asn Gln Gly  Pro Trp Pro
    1235                1240                1245

Phe Ile  Gly Leu Asn Leu Pro  Asp Leu Leu Asp Arg  Arg Val Arg
    1250                1255                1260

Leu Val  Ser Arg Pro Ala Ser  Ala Ser Thr Ala Ala  Gly Ser Met
    1265                1270                1275

Lys Arg  His Ala Ala Glu Gln  Asp Val Leu Leu Lys  Gln Ala Phe
    1280                1285                1290

Ala Arg  Lys
    1295

<210> SEQ ID NO 5
<211> LENGTH: 1274
<212> TYPE: PRT
<213> ORGANISM: Kibdelosporangium phytohabitans

<400> SEQUENCE: 5

Met Gly Ser Ser His His His His His His Ser Ser Gly Leu Val Pro
1               5                   10                  15

Arg Gly Ser His Met Met Ala Arg Ile Arg Leu Met Ser Ser Ser Ser
            20                  25                  30

Pro Ala Ser Gln Phe Gly Pro Asn Glu Trp Leu Val Glu Glu Met Tyr
        35                  40                  45

Glu Gln Phe Leu Ala Asp Pro Ala Ser Val Asp Pro Ala Trp His Asp
    50                  55                  60

Phe Phe Ala Asp Tyr Lys Pro Thr Gln Gln Arg Ala Gln Gly Val Ala
65                  70                  75                  80

Ser Asn Ser Ala Thr Gly Gln Thr Thr Thr Val Thr Lys Ile Glu Pro
                85                  90                  95

Pro Ala Pro Asp Thr Asn Gly Gln Ala Pro Ala Ala Lys Ala Ala Ala
            100                 105                 110

Pro Lys Ala Thr Ala Pro Lys Ala Ala Gln Pro Lys Ala Ser Ala Pro
        115                 120                 125

Ser Ser Ala Pro Pro Lys Pro Thr Thr Lys Pro Thr Lys Pro Ala Thr
    130                 135                 140
```

-continued

```
Pro Ala Ala Lys Lys Pro Glu Pro Ala Lys Ala Ala Pro Gln Ala Glu
145                 150                 155                 160

Gly Asp Thr Ser Lys Pro Ile Arg Gly Ala Ala Ala Ile Ala Lys
                165                 170                 175

Asn Met Glu Gln Ser Leu Thr Val Pro Thr Ala Thr Ser Val Arg Ala
            180                 185                 190

Val Pro Ala Lys Leu Leu Phe Asp Asn Arg Val Val Ile Asn Asn Arg
        195                 200                 205

Leu Arg Arg Thr Arg Gly Gly Lys Ile Ser Phe Thr His Leu Ile Gly
    210                 215                 220

Tyr Ala Leu Val Arg Ala Leu Lys Asp Tyr Pro Asn Met Asn Arg His
225                 230                 235                 240

Tyr Ala Ala Ala Asp Gly Lys Pro Gln Leu Val Thr Pro Glu His Val
                245                 250                 255

Asn Leu Gly Leu Ala Ile Asp Leu Pro Gly Lys Asp Gly Ala Arg Asn
            260                 265                 270

Leu Val Val Ala Ser Ile Lys Gly Cys Glu Glu Met Thr Phe Ala Gln
        275                 280                 285

Phe Trp Gln Ala Tyr Glu Asp Leu Ile Arg Lys Ala Arg Gly Gly Asn
    290                 295                 300

Leu Gly Thr Glu Asp Phe Ala Gly Thr Thr Ile Ser Leu Thr Asn Pro
305                 310                 315                 320

Gly Thr Ile Gly Thr Asn His Ser Val Pro Arg Leu Thr Ala Gly Gln
                325                 330                 335

Gly Ala Ile Ile Gly Val Gly Ala Met Glu Tyr Pro Ala Gln Tyr Gln
            340                 345                 350

Gly Thr Ser Glu Lys Ala Leu Val Glu Met Gly Ile Ser Lys Ile Met
        355                 360                 365

Thr Leu Thr Ser Thr Tyr Asp His Arg Ile Ile Gln Gly Ala Glu Ser
    370                 375                 380

Gly Glu Phe Leu Arg Arg Ile His Gln Leu Leu Leu Gly Glu Asp Lys
385                 390                 395                 400

Phe Tyr Asp Asp Val Phe Thr Ser Leu Arg Ile Pro Tyr Glu Pro Ile
                405                 410                 415

Arg Trp Val Gln Asp Ile Pro Glu Gly Thr Leu Asp Lys Ala Ala Arg
            420                 425                 430

Val Ile Glu Leu Ile Asp Ala Phe Arg Asn Arg Gly His Leu Met Ala
        435                 440                 445

Asp Thr Asp Pro Leu Asn Tyr Arg Gln Arg Arg His Asp Asp Leu Asp
    450                 455                 460

Ile Leu Ser His Gly Leu Thr Leu Trp Asp Leu Asp Arg Glu Phe Ala
465                 470                 475                 480

Val Gly Gly Phe Ala Gly Gln Glu Arg Met Lys Leu Arg Asp Val Leu
                485                 490                 495

Ser Val Leu Arg Asp Ser Tyr Cys Arg Thr Val Gly Ile Glu Tyr Thr
            500                 505                 510

His Ile Leu Asp Pro Ala Glu Arg Arg Trp Ile Gln Asp Arg Val Glu
        515                 520                 525

Ile Pro His Glu Lys Pro Asp Ala Ala Val Gln Lys Tyr Ile Leu Ser
    530                 535                 540

Lys Leu Asn Ala Ala Glu Ala Phe Glu Thr Phe Leu Gln Thr Lys Tyr
545                 550                 555                 560

Val Gly Gln Lys Arg Phe Ser Leu Glu Gly Gly Glu Ser Val Ile Pro
```

-continued

```
                565                     570                     575
Leu Leu Asp Thr Ile Leu Asp Lys Ala Ala Glu Ala Glu Leu Asp Glu
            580                 585                 590

Val Val Ile Gly Met Pro His Arg Gly Arg Leu Asn Val Leu Ala Asn
            595                 600                 605

Ile Val Gly Lys Pro Ile Ser Gln Ile Phe Arg Glu Phe Glu Gly Asn
        610                 615                 620

Leu Asp Pro Gly Gln Ala His Gly Ser Gly Asp Val Lys Tyr His Leu
625                 630                 635                 640

Gly Ala Glu Gly Lys Tyr Phe Arg Met Phe Gly Asp Gly Glu Thr Lys
                645                 650                 655

Val Ser Leu Thr Ala Asn Pro Ser His Leu Glu Thr Val Asp Pro Val
            660                 665                 670

Leu Glu Gly Ile Val Arg Ala Lys Gln Asp Ile Leu Asp Lys Gly Gly
            675                 680                 685

Glu Gly Phe Thr Val Leu Pro Val Ala Leu His Gly Asp Ala Ala Phe
        690                 695                 700

Ala Gly Gln Gly Val Val Ala Glu Thr Leu Asn Leu Ala Leu Leu Arg
705                 710                 715                 720

Gly Tyr Arg Thr Gly Gly Thr Val His Val Ile Ile Asn Asn Gln Val
                725                 730                 735

Gly Phe Thr Thr Ala Pro Glu His Ser Arg Ser Ser Gln Tyr Ala Thr
            740                 745                 750

Asp Val Ala Lys Met Ile Gln Ala Pro Val Phe His Val Asn Gly Asp
            755                 760                 765

Asp Pro Glu Ala Cys His Trp Val Ala Arg Leu Ala Met Asp Tyr Arg
        770                 775                 780

Gln Ala Phe Asn Lys Asp Val Val Ile Asp Met Leu Cys Tyr Arg Arg
785                 790                 795                 800

Arg Gly His Asn Glu Gly Asp Asp Pro Ser Met Thr Gln Pro Ala Met
                805                 810                 815

Tyr Asp Ile Ile Asp Thr Lys Arg Ser Val Arg Lys Thr Tyr Thr Glu
            820                 825                 830

Ala Leu Ile Gly Arg Gly Asp Ile Ser Val Asp Glu Ala Glu Lys Ala
            835                 840                 845

Leu Arg Asp Phe Ser Ser Gln Leu Glu His Val Phe Asn Glu Val Arg
        850                 855                 860

Glu Leu Glu Lys His Pro Pro Val Pro Ser Pro Ser Val Glu Glu Glu
865                 870                 875                 880

Gln Gln Val Pro Ala Arg Val Pro Thr Ala Val Ala Arg Glu Val Ile
                885                 890                 895

Glu Arg Ile Ala Asp Ala His Ile Asn Leu Pro Glu Gly Phe Thr Pro
            900                 905                 910

His Pro Arg Val Lys Pro Val Leu Glu Arg Arg Ala Lys Met Ala Arg
            915                 920                 925

Glu Gly Asp Ile Asp Trp Ala Phe Gly Glu Leu Leu Ala Phe Gly Ser
        930                 935                 940

Leu Asn Leu Glu Gly Lys Leu Val Arg Leu Ala Gly Gln Asp Ser Arg
945                 950                 955                 960

Arg Gly Thr Phe Val Gln Arg His Ser Val Val Val Asp Arg Lys Thr
                965                 970                 975

Gly Gln Glu Tyr Thr Pro Leu Gln Asn Leu Ser Glu Asp Gln Gly Arg
            980                 985                 990
```

```
Phe Met Val Tyr Asp Ser Ala Leu  Ser Glu Tyr Ala Ala  Val Gly Phe
        995                1000                 1005

Glu Tyr  Gly Tyr Ser Val Ala  Asn Gly Asp Ala Leu  Val Leu Trp
    1010                1015                 1020

Glu Ala  Gln Phe Gly Asp Phe  Val Asn Gly Ala Gln  Ser Val Ile
    1025                1030                 1035

Asp Glu  Phe Ile Ser Ser Ser  Glu Ala Lys Trp Gly  Gln Leu Ser
    1040                1045                 1050

Asp Val  Val Leu Leu Leu Pro  His Gly His Glu Gly  Gln Gly Pro
    1055                1060                 1065

Asp His  Thr Ser Gly Arg Ile  Glu Arg Trp Leu Gln  Leu Cys Ala
    1070                1075                 1080

Glu Gly  Ser Met Thr Val Ala  Ile Pro Ser Thr Pro  Ala Asn Tyr
    1085                1090                 1095

Phe His  Leu Leu Arg Arg His  Ala Leu Asp Gly Val  Thr Arg Pro
    1100                1105                 1110

Leu Ile  Val Phe Thr Pro Lys  Ser Met Leu Arg Asn  Lys Ala Ala
    1115                1120                 1125

Val Ser  Pro Val Glu Asp Phe  Thr Asn Asn Lys Phe  Met Ser Val
    1130                1135                 1140

Leu Asp  Asp Pro Thr Gln Pro  Asp Pro Gln Gly Val  Arg Lys Ile
    1145                1150                 1155

Leu Phe  Val Ser Gly Lys Leu  Tyr Tyr Glu Leu Ala  Ala Glu Gln
    1160                1165                 1170

Ala Lys  Arg Gly Val Thr Asp  Thr Ala Ile Val Arg  Val Glu Gln
    1175                1180                 1185

Leu Tyr  Pro Val Pro Gln Lys  Lys Leu Gly Leu Ile  Phe Glu Arg
    1190                1195                 1200

Tyr Pro  Asn Ala His Asp Val  Arg Trp Val Gln Glu  Glu Pro Ala
    1205                1210                 1215

Asn Gln  Gly Ser Trp Pro Phe  Tyr Gly Leu Phe Val  Arg Glu Lys
    1220                1225                 1230

Phe Pro  Glu Arg Met Gly Thr  Met Lys Arg Val Ser  Arg Arg Pro
    1235                1240                 1245

Met Ala  Ala Pro Ser Val Gly  Ser Ser Lys Val His  Glu Val Glu
    1250                1255                 1260

Gln Arg  Glu Leu Ile Glu Lys  Ala Phe Ala Asp
    1265                1270
```

```
<210> SEQ ID NO 6
<211> LENGTH: 446
<212> TYPE: PRT
<213> ORGANISM: Escherichia coli

<400> SEQUENCE: 6
```

```
Met Gly Ser Ser His His His  His His His Ser Ser Gly Leu Val Pro
1                5                 10                 15

Arg Gly Ser His Met Asn Ser  Asn Lys Glu Leu Met Gln Arg Arg Ser
            20                25                 30

Gln Ala Ile Pro Arg Gly Val  Gly Gln Ile His Pro Ile Phe Ala Asp
        35                40                 45

Arg Ala Glu Asn Cys Arg Val  Trp Asp Val Glu Gly Arg Glu Tyr Leu
    50                55                 60

Asp Phe Ala Gly Gly Ile Ala  Val Leu Asn Thr Gly His Leu His Pro
```

```
65                  70                  75                  80

Lys Val Val Ala Ala Val Glu Ala Gln Leu Lys Lys Leu Ser His Thr
                85                  90                  95

Cys Phe Gln Val Leu Ala Tyr Glu Pro Tyr Leu Glu Leu Cys Glu Ile
                100                 105                 110

Met Asn Gln Lys Val Pro Gly Asp Phe Ala Lys Lys Thr Leu Leu Val
                115                 120                 125

Thr Thr Gly Ser Glu Ala Val Glu Asn Ala Val Lys Ile Ala Arg Ala
        130                 135                 140

Ala Thr Lys Arg Ser Gly Thr Ile Ala Phe Ser Gly Ala Tyr His Gly
145                 150                 155                 160

Arg Thr His Tyr Thr Leu Ala Leu Thr Gly Lys Val Asn Pro Tyr Ser
                165                 170                 175

Ala Gly Met Gly Leu Met Pro Gly His Val Tyr Arg Ala Leu Tyr Pro
                180                 185                 190

Cys Pro Leu His Gly Ile Ser Glu Asp Asp Ala Ile Ala Ser Ile His
                195                 200                 205

Arg Ile Phe Lys Asn Asp Ala Ala Pro Glu Asp Ile Ala Ala Ile Val
        210                 215                 220

Ile Glu Pro Val Gln Gly Glu Gly Gly Phe Tyr Ala Ser Ser Pro Ala
225                 230                 235                 240

Phe Met Gln Arg Leu Arg Ala Leu Cys Asp Glu His Gly Ile Met Leu
                245                 250                 255

Ile Ala Asp Glu Val Gln Ser Gly Ala Gly Arg Thr Gly Thr Leu Phe
                260                 265                 270

Ala Met Glu Gln Met Gly Val Ala Pro Asp Leu Thr Thr Phe Ala Lys
        275                 280                 285

Ser Ile Ala Gly Gly Phe Pro Leu Ala Gly Val Thr Gly Arg Ala Glu
        290                 295                 300

Val Met Asp Ala Val Ala Pro Gly Gly Leu Gly Gly Thr Tyr Ala Gly
305                 310                 315                 320

Asn Pro Ile Ala Cys Val Ala Ala Leu Glu Val Leu Lys Val Phe Glu
                325                 330                 335

Gln Glu Asn Leu Leu Gln Lys Ala Asn Asp Leu Gly Gln Lys Leu Lys
                340                 345                 350

Asp Gly Leu Leu Ala Ile Ala Glu Lys His Pro Glu Ile Gly Asp Val
        355                 360                 365

Arg Gly Leu Gly Ala Met Ile Ala Ile Glu Leu Phe Glu Asp Gly Asp
        370                 375                 380

His Asn Lys Pro Asp Ala Lys Leu Thr Ala Glu Ile Val Ala Arg Ala
385                 390                 395                 400

Arg Asp Lys Gly Leu Ile Leu Leu Ser Cys Gly Pro Tyr Tyr Asn Val
                405                 410                 415

Leu Arg Ile Leu Val Pro Leu Thr Ile Glu Asp Ala Gln Ile Arg Gln
                420                 425                 430

Gly Leu Glu Ile Ile Ser Gln Cys Phe Asp Glu Ala Lys Gln
                435                 440                 445
```

<210> SEQ ID NO 7
<211> LENGTH: 453
<212> TYPE: PRT
<213> ORGANISM: Escherichia coli

<400> SEQUENCE: 7

-continued

```
Met Gly Ser Ser His His His His His His Ser Ser Gly Leu Val Pro
1               5                   10                  15

Arg Gly Ser His Met Met Ala Arg Ile Arg Leu Met Asn Ser Asn Lys
            20                  25                  30

Glu Leu Met Gln Arg Arg Ser Gln Ala Ile Pro Arg Gly Val Gly Gln
        35                  40                  45

Ile His Pro Ile Phe Ala Asp Arg Ala Glu Asn Cys Arg Val Trp Asp
    50                  55                  60

Val Glu Gly Arg Glu Tyr Leu Asp Phe Ala Gly Gly Ile Ala Val Leu
65                  70                  75                  80

Asn Thr Gly His Leu His Pro Lys Val Val Ala Ala Val Glu Ala Gln
                85                  90                  95

Leu Lys Lys Leu Ser His Thr Cys Phe Gln Val Leu Ala Tyr Glu Pro
        100                 105                 110

Tyr Leu Glu Leu Cys Glu Ile Met Asn Gln Lys Val Pro Gly Asp Phe
        115                 120                 125

Ala Lys Lys Thr Leu Leu Val Thr Thr Gly Ser Glu Ala Val Glu Asn
        130                 135                 140

Ala Val Lys Ile Ala Arg Ala Ala Thr Lys Arg Ser Gly Thr Ile Ala
145                 150                 155                 160

Phe Ser Gly Ala Tyr His Gly Arg Thr His Tyr Thr Leu Ala Leu Thr
                165                 170                 175

Gly Lys Val Asn Pro Tyr Ser Ala Gly Met Gly Leu Met Pro Gly His
            180                 185                 190

Val Tyr Arg Ala Leu Tyr Pro Cys Pro Leu His Gly Ile Ser Glu Asp
            195                 200                 205

Asp Ala Ile Ala Ser Ile His Arg Ile Phe Lys Asn Asp Ala Ala Pro
    210                 215                 220

Glu Asp Ile Ala Ala Ile Val Ile Glu Pro Val Gln Gly Ser Gly Gly
225                 230                 235                 240

Phe Tyr Ala Ser Ser Pro Ala Phe Met Gln Arg Leu Arg Ala Leu Cys
                245                 250                 255

Asp Glu His Gly Ile Met Leu Ile Ala Asp Glu Val Gln Ser Gly Ala
            260                 265                 270

Gly Arg Thr Gly Thr Leu Phe Ala Met Glu Gln Met Gly Val Ala Pro
        275                 280                 285

Asp Leu Thr Thr Phe Ala Lys Ser Ile Ala Gly Gly Phe Pro Leu Ala
    290                 295                 300

Gly Val Thr Gly Arg Ala Glu Val Met Asp Ala Val Ala Pro Gly Gly
305                 310                 315                 320

Leu Gly Gly Thr Tyr Ala Gly Asn Pro Ile Ala Cys Val Ala Ala Leu
                325                 330                 335

Glu Val Leu Lys Val Phe Glu Gln Glu Asn Leu Leu Gln Lys Ala Asn
            340                 345                 350

Asp Leu Gly Gln Lys Leu Lys Asp Gly Leu Leu Ala Ile Ala Glu Lys
            355                 360                 365

His Pro Glu Ile Gly Asp Val Arg Gly Leu Gly Ala Met Ile Ala Ile
    370                 375                 380

Glu Leu Phe Glu Asp Gly Asp His Asn Lys Pro Asp Ala Lys Leu Thr
385                 390                 395                 400

Ala Glu Ile Val Ala Arg Ala Arg Asp Lys Gly Leu Ile Leu Leu Ser
                405                 410                 415

Cys Gly Pro Tyr Tyr Asn Val Leu Arg Ile Leu Val Pro Leu Thr Ile
```

-continued

```
                420             425             430
Glu Asp Ala Gln Ile Arg Gln Gly Leu Glu Ile Ile Ser Gln Cys Phe
            435             440             445

Asp Glu Ala Lys Gln
    450

<210> SEQ ID NO 8
<211> LENGTH: 368
<212> TYPE: PRT
<213> ORGANISM: Rhodosporidium toruloides

<400> SEQUENCE: 8

Met His Ser Gln Lys Arg Val Val Val Leu Gly Ser Gly Val Ile Gly
1               5                   10                  15

Leu Ser Ser Ala Leu Ile Leu Ala Arg Lys Gly Tyr Ser Val His Ile
            20                  25                  30

Leu Ala Arg Asp Leu Pro Glu Asp Val Ser Ser Gln Thr Phe Ala Ser
            35                  40                  45

Pro Trp Ala Gly Ala Asn Trp Thr Pro Phe Met Thr Leu Thr Asp Gly
    50                  55                  60

Pro Arg Gln Ala Lys Trp Glu Glu Ser Thr Phe Lys Lys Trp Val Glu
65                  70                  75                  80

Leu Val Pro Thr Gly His Ala Met Trp Leu Lys Gly Thr Arg Arg Phe
                85                  90                  95

Ala Gln Asn Glu Asp Gly Leu Leu Gly His Trp Tyr Lys Asp Ile Thr
            100                 105                 110

Pro Asn Tyr Arg Pro Leu Pro Ser Ser Glu Cys Pro Pro Gly Ala Ile
            115                 120                 125

Gly Val Thr Tyr Asp Thr Leu Ser Val His Ala Pro Lys Tyr Cys Gln
    130                 135                 140

Tyr Leu Ala Arg Glu Leu Gln Lys Leu Gly Ala Thr Phe Glu Arg Arg
145                 150                 155                 160

Thr Val Thr Ser Leu Glu Gln Ala Phe Asp Gly Ala Asp Leu Val Val
                165                 170                 175

Asn Ala Thr Gly Leu Gly Ala Lys Ser Ile Ala Gly Ile Asp Asp Gln
            180                 185                 190

Ala Ala Glu Pro Ile Arg Gly Gln Thr Val Leu Val Lys Ser Pro Cys
            195                 200                 205

Lys Arg Cys Thr Met Asp Ser Ser Asp Pro Ala Ser Pro Ala Tyr Ile
    210                 215                 220

Ile Pro Arg Pro Gly Gly Glu Val Ile Cys Gly Gly Thr Tyr Gly Val
225                 230                 235                 240

Gly Asp Trp Asp Leu Ser Val Asn Pro Glu Thr Val Gln Arg Ile Leu
                245                 250                 255

Lys His Cys Leu Arg Leu Asp Pro Thr Ile Ser Ser Asp Gly Thr Ile
            260                 265                 270

Glu Gly Ile Glu Val Leu Arg His Asn Val Gly Leu Arg Pro Ala Arg
            275                 280                 285

Arg Gly Gly Pro Arg Val Glu Ala Glu Arg Ile Val Leu Pro Leu Asp
    290                 295                 300

Arg Thr Lys Ser Pro Leu Ser Leu Gly Arg Gly Ser Ala Arg Ala Ala
305                 310                 315                 320

Lys Glu Lys Glu Val Thr Leu Val His Ala Tyr Gly Phe Ser Ser Ala
                325                 330                 335
```

-continued

```
Gly Tyr Gln Gln Ser Trp Gly Ala Ala Glu Asp Val Ala Gln Leu Val
            340                 345                 350

Asp Glu Ala Phe Gln Arg Tyr His Gly Ala Ala Arg Glu Ser Lys Leu
            355                 360                 365
```

METHODS FOR IMPROVING YIELDS OF L-GLUFOSINATE

CROSS-REFERENCE TO PRIORITY APPLICATION

This application is a National Stage application of International Application No. PCT/US2019/049467, filed Sep. 4, 2019, which claims priority to U.S. Patent Application No. 62/727,322, filed Sep. 5, 2018.

INCORPORATION BY REFERENCE OF MATERIAL SUBMITTED ELECTRONICALLY

The Sequence Listing, which is a part of the present disclosure, is submitted concurrently with the specification as a text file. The name of the text file containing the Sequence Listing is "M2026499_Seqlisting.txt", which was created on Feb. 16, 2021 and is 64,418 bytes in size. The subject matter of the Sequence Listing is incorporated herein in its entirety by reference.

FIELD

Described herein are methods for producing L-glufosinate in high yield.

BACKGROUND

The herbicide glufosinate is a non-selective, foliarly-applied herbicide considered to be one of the safest herbicides from a toxicological or environmental standpoint. Current commercial chemical synthesis methods for glufosinate yield a racemic mixture of L-and D-glufosinate (Duke et al. 2010 Toxins 2:1943-1962). However, L-glufosinate (also known as phosphinothricin or(S)-2-amino-4-(hydroxy (methyl) phosphonoyl) butanoic acid) is much more potent than D-glufosinate (Ruhland et al. (2002) Environ. Biosafety Res. 1:29-37).

Therefore, methods are needed to produce only or primarily the active, L-glufosinate form. While a number of methods to generate pure L-glufosinate, or a mixture of D- and L-glufosinate enriched for L-glufosinate, have been described, cost effective methods to generate high yields of L-glufosinate from racemic glufosinate have not been available.

SUMMARY

Described herein are new and cost-effective methods for the production of L-glufosinate in high yield. The methods involve converting racemic glufosinate to the L-glufosinate enantiomer. In particular, the methods involve the specific amination of PPO (2-ox0-4-(hydroxy (methyl) phosphinoyl) butyric acid) to L-glufosinate, using L-glutamate, racemic glutamate, or another amine source as an amine donor. PPO can be obtained by the oxidative deamination of D-glufosinate to PPO or generated via chemical synthesis. PPO is then converted to L-glufosinate using a transaminase in the presence of an amine donor. When the amine donor donates an amine to PPO, L-glufosinate and a reaction by-product are formed. For example, when the amine donor is glutamate (including racemic glutamate or L-glutamate), L-glufosinate and the reaction by-product α-ketoglutarate (KG), also known as oxoglutarate, are produced.

The transamination reaction is an equilibrium reaction, which means that under certain conditions, some PPO will remain when the reaction is at equilibrium. The PPO so remaining represents a yield loss of L-glufosinate, and thus it is desirable to minimize the amount of PPO remaining in the reaction mixture. Degradation, other chemical modification, extraction, sequestration, binding, or other methods to reduce the effective concentration of the by-product, i.e., the corresponding alpha ketoacid or ketone to the chosen amine donor, will shift the reaction equilibrium toward L-glufosinate, thereby reducing the amount of PPO and increasing the yield of L-glufosinate. Therefore, the methods described herein involve the conversion or elimination of the alpha ketoacid or ketone by-product to another product to shift the equilibrium towards L-glufosinate. The alpha ketoacid or ketone by-product can be converted by enzymatic or chemical means. The alpha ketoacid or ketone by-product can be reduced or eliminated by means such as ion exchange, size exclusion, or other resin. For example, when L-glutamate is used as the amine donor, the KG by-product can be converted to succinic semialdehyde (SSA) by the addition of a ketoglutarate decarboxylase (KGD) to the reaction. The reduction in the amount of KG available for conversion by the transaminase can lead to higher yields of L-glufosinate. If a product is generated by the reduction in amount or elimination of the by-product, it is called the conversion product. For example, if KG is the by-product and a KGD is used to reduce in amount or eliminate the KG, the conversion product is SSA.

Compositions described herein can comprise L-glufosinate and a conversion product. As discussed, where glutamate is used as the amine donor, KG is the by-product and SSA is the conversion product. In such compositions, L-glufosinate is present at a molar amount of 0.5 times to 1,000 times the molar amount of SSA or another conversion product.

Other compositions comprise L-glufosinate, PPO, and SSA. In such compositions, PPO is present at less than 10% of the amount of L-glufosinate and the conversion product is present at a molar amount up to 2 times the amount of L-glufosinate.

Also described herein is a method for selectively controlling weeds. In one embodiment, the method is useful for controlling weeds in a field containing a crop of planted seeds or crops that are optionally resistant to glufosinate. The method comprises applying an effective amount of a composition comprising L-glufosinate at an enantiomeric excess of greater than 90% over D-glufosinate to the field. Such methods of use include selectively controlling weeds in a field, controlling weeds in non-field areas, defoliating plants or crops, and/or desiccating crops before harvest, comprising applying an effective amount of a composition comprising L-glufosinate at an enantiomeric excess of greater than 90% over D-glufosinate and more than 0.01% but less than 10% PPO and less than about 10% of the ketone byproduct. In one embodiment, the composition comprises greater than 90% L-glufosinate, less than 10% PPO, and less than 10% of the ketone byproduct conversion product relative to the amount of L-glufosinate. In some embodiments, the ketone byproduct conversion product is SSA.

The details of one or more embodiments are set forth in the drawings and the description below. Other features, objects, and advantages will be apparent from the description and drawings, and from the claims.

DETAILED DESCRIPTION

Figure 1:
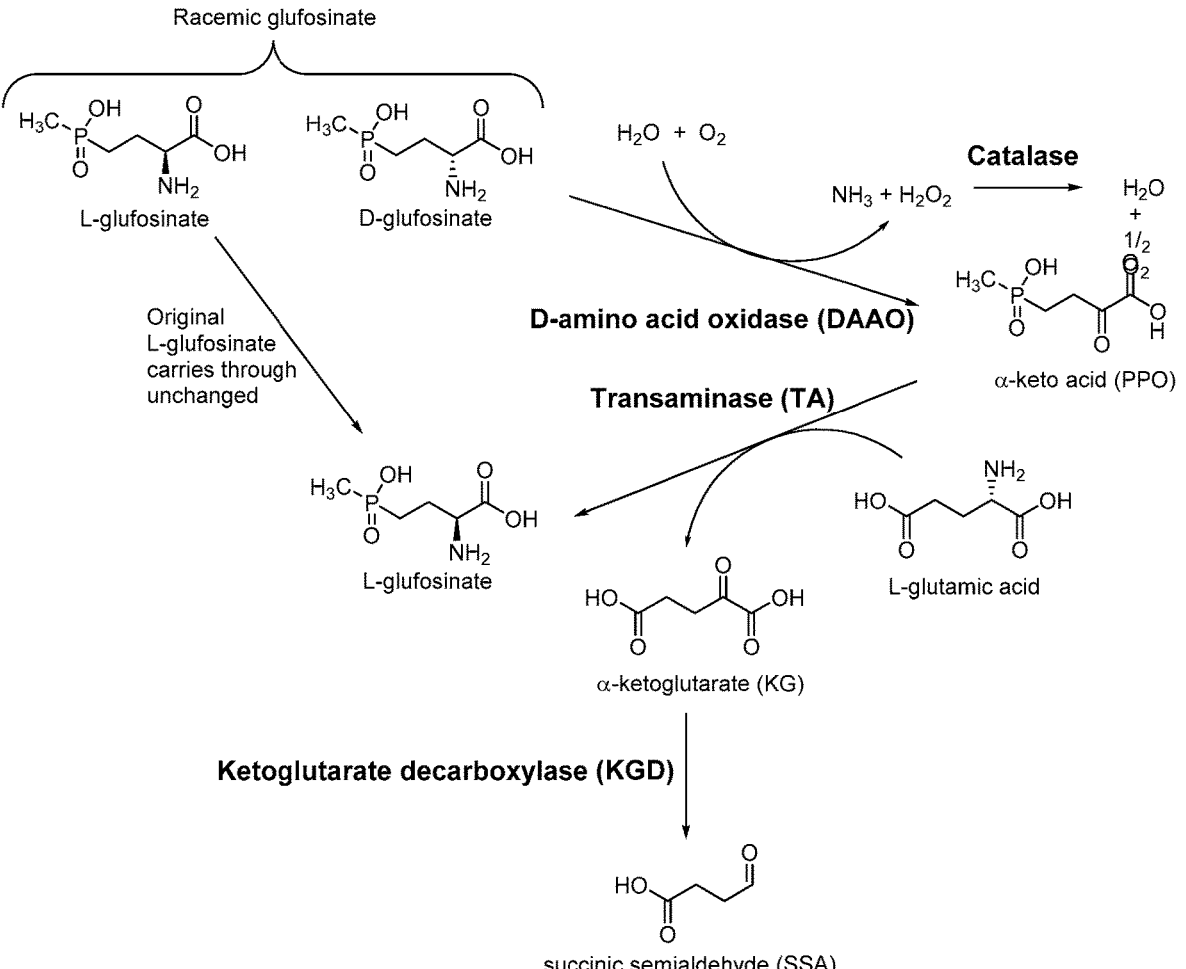
FIG. 1 is a schematic of an exemplary conversion of racemic glufosinate to L-glufosinate using L-glutamate as an amine donor and a ketoglutarate decarboxylase (KGD) as the method to reduce the amount of KG.

Compositions and methods for the production of L-glufosinate (also known as phosphinothricin or(S)-2-amino-4-(hydroxy (methyl) phosphonoyl) butanoic acid) are provided. In particular, the methods described herein increase the yield of L-glufosinate or simplify the isolation of L-glufosinate from the reaction mass. When the starting material for the production of substantially purified L-glufosinate is racemic glufosinate, the methods comprise a three-step process, which may occur in a single vessel and nearly simultaneously, in multiple vessels and sequentially, or in multiple vessels and nearly simultaneously.

U.S. Pat. No. 9,834,802, herein incorporated by reference, describes a two-step method for the production of L-glufosinate comprising reacting D-glufosinate with a D-amino acid oxidase (DAAO) enzyme to form PPO (2-oxo-4-(hydroxy (methyl) phosphinoyl) butyric acid): followed by aminating the PPO to L-glufosinate by a transaminase (TA) enzyme, using an amine group from one or more amine donors. The reaction of PPO with a transaminase results in the production of L-glufosinate and a by-product, the corresponding alpha ketoacid or ketone, depending upon the chosen amine donor. Suitable amine donors include L-aspartate or racemic aspartate, L-glutamate or racemic glutamate, L-alanine or racemic alanine, L-1-phenylethylamine or racemic 1-phenylethylamine, L-phenylalanine or racemic phenylalanine, phenylethylamine, L-glycine or racemic glycine, L-lysine or racemic lysine, L-valine or racemic valine, L-serine or racemic serine, L-glutamine or racemic glutamine, isopropylamine, sec-butylamine, ethanolamine, 2-aminobutyric acid, and diaminopropionic acid.

The present method adds a third step to the method set forth in U.S. Pat. No. 9,834,802, described above, that involves reducing the effective levels of the alpha ketoacid by-product generated during the second step of amination of PPO to L-glufosinate. The by-product of the second step can be removed by enzymatic or chemical conversion, by physical removal such as ion exchange, size exclusion, and the like. Without being bound by theory, it is thought that by reducing the effective levels of the by-product of the second step, the second reaction can continue at a higher rate and/or reach equilibrium concentrations that result in a higher yield of L-glufosinate. By combining these reactions, the proportion of L-glufosinate can be substantially increased in a racemic glufosinate mixture. Thus, provided herein are methods to obtain a composition substantially comprising L-glufosinate. For purposes of the methods and compositions described herein, a composition comprising substantially L-glufosinate contains less than 10% PPO, less than 5% PPO, less than 2% PPO, less than 1% PPO, contains at least 0.01% PPO, or contains no detectable PPO, relative to the amount of L-glufosinate. Additionally, the composition comprises an amount of the $\alpha$-ketoacid or ketone by-product (for example, KG). For purposes of the methods and compositions described herein, a composition comprising substantially L-glufosinate contains less than 50% by-product, less than 25% by-product, less than 10% by-product, less than 5% by-product, less than 2% by-product, less than 1% by-product, or contains no detectable by-product, relative to the amount of L-glufosinate. Reduction in the amount of the by-product results in increasing levels of the conversion product. Therefore, the composition may comprise at least 5% conversion product, at least 10% conversion product, at least 25% conversion product, at least 50% conversion product, at least 75% conversion product, at least 100% conversion, or at least 200% conversion product relative to the amount of L-glufosinate. Since L-glufosinate is more potent than D-glufosinate, smaller amounts of the composition are needed to be effective as an herbicide.

The methods described herein provide an efficient method for the conversion of PPO to L-glufosinate, particularly when a transaminase is used in the reaction. As discussed, the transaminase produces L-glufosinate and an alpha ketoacid or ketone by-product. The methods described herein provide for the reduction of the alpha ketoacid or ketone by-product to drive the reaction towards L-glufosinate, reducing the amount of PPO. A number of amine donors can be used in the reaction. If glutamate or L-glutamate is the amine donor, the by-product would be the alpha ketoacid KG. If isopropylamine is the amine donor, the by-product would be the ketone acetone. If alanine is the amine donor, the by-product would be the alpha ketoacid pyruvate. If sec-butylamine is the amine donor, the by-product would be the ketone 2-butanone. If phenylethylamine is the amine donor, the by-product would be the ketone acetophenone. If lysine is the amine donor, the by-product would be the alpha ketoacid hexanoic acid or the semialdehyde 2-aminoadipate-6-semialdehyde. If aspartate is the amine donor, the by-product would be the alpha ketoacid oxaloacetate. If glycine is the amine donor, the by-product would be the alpha ketoacid glyoxylate. If valine is the amine donor, the by-product would be the alpha ketoacid alpha ketoisovaleric acid. If serine is the amine donor, the by-product would be the alpha ketoacid 3-hydroxypyruvate. If glutamine is the amine donor, the by-product would be the alpha ketoacid 2-oxoglutaramate. If ethanolamine is the amine donor, the by-product would be the aldehyde glycolaldehyde. If 2-aminobutyric acid is the amine donor, the by-product would be the alpha ketoacid 2-oxobutanoic acid. If diaminoproprionic acid is the amine donor, the by-product would be the alpha ketoacid 3-amino-2-oxopropanoic acid or the semialdehyde 3-oxoalanine.

In one embodiment, the first step is catalyzed by a D-amino acid oxidase (DAAO) enzyme and the second step is catalyzed by a transaminase (TA) enzyme and glutamate is utilized by the TA enzyme as the amine donor. The by-product produced is $\alpha$-ketoglutarate (KG). In this embodiment, a ketoglutarate decarboxylase (KGD) enzyme can be used, for example, (EC 4.1.1.71). Without intending to be limiting. SEQ ID NO: 1 through SEQ ID NO: 5 are example KGD enzymes. The ketoglutarate decarboxylase converts KG to carbon dioxide and succinic semialdehyde (SSA). FIG. 1 contains a schematic of this exemplary reaction. While the methods can be used to produce a substantially purified L-glufosinate in a batch reaction, it is recognized that a continuous process can be used.

One embodiment, described herein, is a composition comprising a mixture of L-glufosinate and SSA. Initially, the amount of L-glufosinate will be much higher than the amount of SSA. As the reaction proceeds, the amount of SSA increases, and could reach as high as the amount of L-glufosinate, or even higher. Compositions of L-glufosinate may comprise L-glufosinate and SSA, with the molar amount of L-glufosinate being 0.5 times to 1,000 times the amount of SSA. These compositions can optionally occur as dried powders or dissolved in aqueous or non-aqueous carriers and additional chemical species can optionally be present. Optionally, the composition is prepared and used in an ex vivo environment.

It is also recognized that the L-glufosinate can be further isolated and used in formulations as an herbicide. In many of the reactions to generate L-glufosinate that are known in the art, the post-reaction mixture contains a number of additional components, often times at significant levels relative to L-glufosinate. The complexity of these mixtures can make it difficult and or costly to isolate the L-glufosinate. In the case of the reactions described in U.S. Pat. No. 9,834,802, the post-reaction mixtures typically include L-glufosinate, KG, PPO, and glutamic acid. Isolation of L-glufosinate in the post-reaction mixture typically requires multiple operations because the chemical structures and chemical properties of these components are very similar. L-glutamic acid presents the main challenge because it is present in a high concentration relative to L-glufosinate and is structurally similar to L-glufosinate. In the International PCT Patent Application PCT/US2018/042503, "Methods for the Purification of L-Glufosinate," incorporated herein by reference in its entirety, improved methods of isolation are described, but even simpler isolation would be preferred. It is recognized that the reactions embodied here could have lower levels of KG, PPO, and glutamic acid, and higher levels of L-glufosinate, than the reactions described in U.S. Pat. No. 9,834,802, and that this could simplify the isolation of L-glufosinate.

I. Methods of Synthesis

Methods for the conversion of D-glufosinate to L-glufosinate at high yield in an ex vivo environment are provided. The methods described herein provide a means for converting a low-cost feedstock of a racemic mixture of D- and L-glufosinate into a more valuable product that has been enriched for L-glufosinate.

FIG. 1 shows an exemplary schematic of one embodiment described herein. In this example, a DAAO enzyme, a TA enzyme, and a ketoglutarate decarboxylase (KGD) enzyme are combined, optionally with a catalase enzyme, to catalyze several reactions that lead to an enrichment of L-glufosinate from racemic glufosinate. These reactions could occur in one, or more than one, reaction vessel, including in batch or flow reaction modes. These enzymes could be added at the same time (including by co-immobilization to a solid support) or at different times as desired.

If the reaction shown in FIG. 1 does not contain the KGD enzyme, approximately 3-4 times as many moles of glutamate as moles of racemic glufosinate are required at the start of the reaction to bias the equilibrium sufficiently toward L-glufosinate that yield losses to PPO are less than 10% (see U.S. Pat. No. 9,834,802). When the effective levels of KG available to the TA are reduced, as in the methods described herein, the equilibrium is more biased toward L-glufosinate. In fact, complete conversion of PPO to L-glufosinate could be obtained with an equivalent number of moles of glutamate as moles of PPO (which is half the number of moles of racemic glufosinate before the DAAO enzyme catalyzes the oxidative deamination of the D-glufosinate) if the KGD enzyme is able to completely, and solely, catalyze the decarboxylation of KG to SSA and if SSA is not a substrate for the TA enzyme. This reaction could completely consume the input glutamate, the by-product KG, and convert all produced PPO to L-glufosinate. The final reaction mass could include SSA at 0.5 times the molar amount of L-glufosinate and no other major organic non-enzymatic reaction components. This simplified reaction mass would clearly provide advantages for purification and isolation of L-glufosinate.

Ketoglutarate decarboxylase (KGD) enzymes (EC 4.1.1.71) catalyze the conversion of KG to carbon dioxide and SSA. KGD enzymes are well known in the art and can be found in a wide range of organisms, including *M. smegmatis*, S, apiospermum, M. maritypicum, A. enclensis, and K. phytohabitans. Without intending to be limiting, SEQ ID NO: 1 through SEQ ID NO:5 are example KGD enzymes. In a preferred embodiment, the KGD enzyme is based on the KGD enzyme from A. enclensis. Since KG is an α-ketoacid and PPO is an α-ketoacid and the decarboxylation occurs from the carboxylic acid at the same end of these relatively similar molecules, it is preferred to utilize a KGD enzyme that rapidly decarboxylases KG but does not efficiently catalyze the decarboxylation of PPO. It may be useful to use various enzyme improvement techniques well known in the art to improve the efficiency of catalysis of the decarboxylation of KG, reduce the efficiency of catalysis of the decarboxylation of PPO, or both. KGD enzymes are examples of a broader class of carboxy-lyase enzymes, as represented by all of the E.C. numbers starting with 4.1.1, and any of those carboxy-lyase enzymes could represent enzymes that could reduce the amount of the by-product and provide the advantages described herein.

In some embodiments, the SSA is sequestered from the reaction mass. This could be preferred to avoid unwanted reactivity of SSA with other reaction components, to enhance the rate of conversion of KG to SSA, or to initiate the purification and isolation of L-glufosinate. SSA can be removed by methods known in the art such as binding to a resin (such as an amine resin, ion exchange resin, size exclusion resin, or other resin), conversion to an oxime (such as with a hydroxylamine derivative) with optional precipitation, reduction (such as with NaBH4), polymerization, or oxidization. SSA that has been produced by a KGD enzyme can be further oxidized to succinic acid, an important chemical intermediate.

Figure 2:
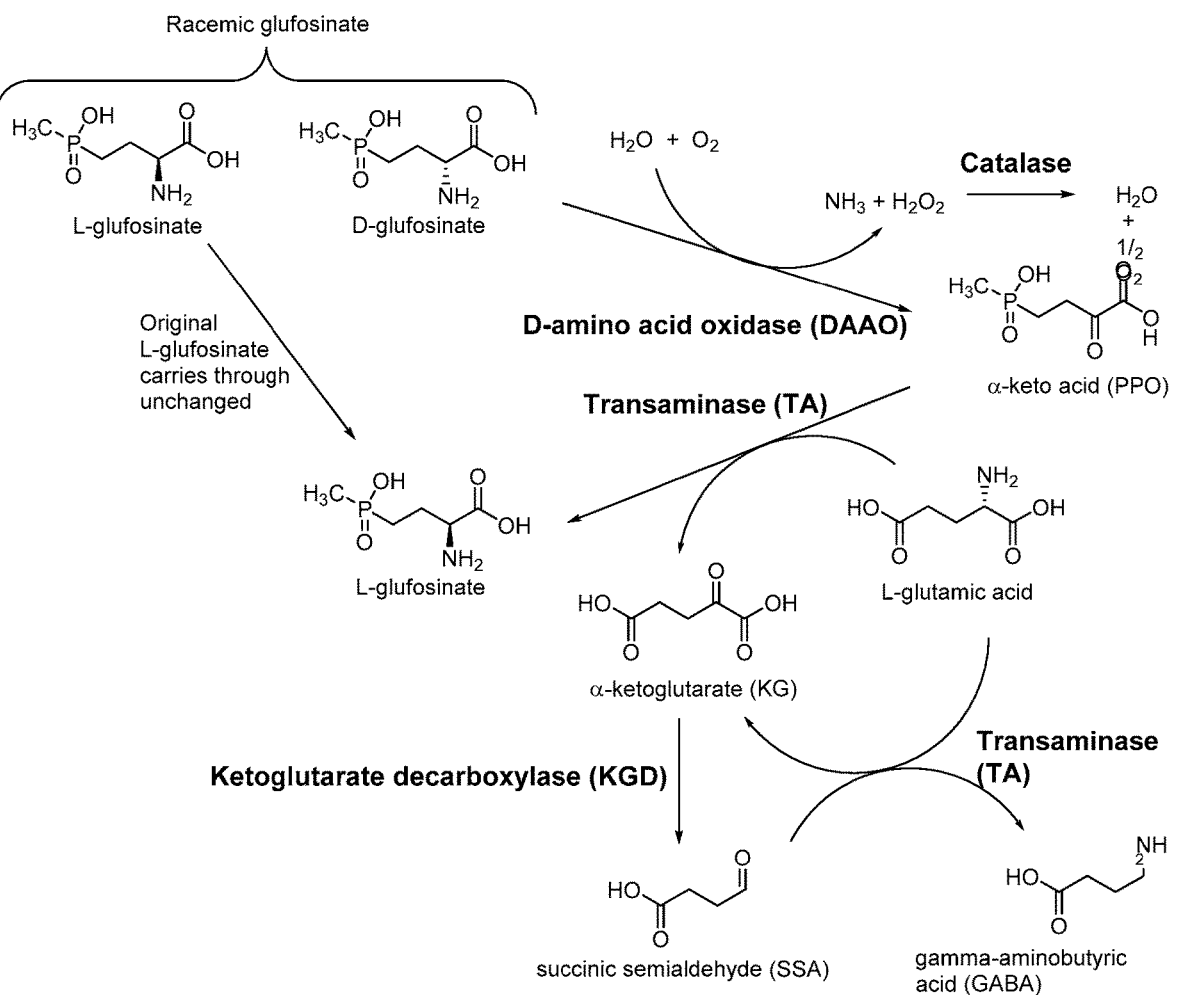
FIG. 2 is a schematic of the reaction in FIG. 1 if the chosen transaminase (TA) is capable of converting L-glutamate and SSA to KG and gamma-aminobutyric acid (GABA); if the TA is capable of this conversion at a high rate relative to the conversion of PPO and L-glutamate to KG and L-glufosinate, the method will not yield high levels of L-glufosinate.

Decarboxylation of KG to SSA is intended to reduce the effective concentration of KG available to the TA and thereby shift the reaction equilibrium toward L-glufosinate and KG from PPO and glutamate. It is possible, however, that SSA could be utilized by enzymes in the reaction mass other that the KGD enzyme. In fact, the reaction natively catalyzed by the *E. coli* gabT TA enzyme commonly utilized in U.S. Pat. No. 9,834,802 is to convert SSA and L-glutamate to KG and gamma-aminobutyric acid (GABA). FIG. 2 shows a schematic of this reaction as part of the full L-glufosinate deracemization reaction. Without being bound be theory, it is thought that such a reaction, when combined with the reaction catalyzed by a KGD enzyme, could eventually lead to depletion of glutamate and accumulation of GABA. This could lead to increased levels of PPO and decreased levels of L-glufosinate, which is counter to the objectives described herein.

In a preferred embodiment, TA enzymes or enzyme mutants or variants are used that do not efficiently utilize the conversion product that is generated by the reduction in amount or elimination of the by-product produced when L-glufosinate is aminated. Mutant variants of gabT have been described that demonstrate varying affinities for substrates including SSA (Liu et al., Biochemistry 2005, 44, 2982-2992). In a preferred embodiment, TA enzymes that do not efficiently catalyze the conversion of SSA and glutamate to KG and GABA, but do efficiently catalyze the conversion of PPO and glutamate to KG and L-glufosinate, are used. In a more preferred embodiment, an E211S mutation in the *E. coli* gabT TA enzyme (SEQ ID NO: 6 is the wild type TA enzyme with leader sequence, SEQ ID NO:7 is the E211S mutant TA enzyme with leader sequence) is used. Sequence homology can be used to identify enzymes or mutations that would be expected to confer the desired substrate specificity. For example, the top 100 sequences found via a blastp search of the NCBI non-redundant sequence database on Aug. 31, 2018 with the wild type *E. coli* gabT TA enzyme sequence, excluding all hits from Enterobacteraceae, yielded sequences from 6 genus. Despite sequence identity as low at 76% compared to the *E. coli* gabT TA enzymes sequence among these hits (GenBank accession number CUJ92856.1 is 100%, KKF68526.1 is 91%, WP_061553513.1 is 89%, WP_025801403.1 is 89%, WP_074941369.1 is 76%, and PRD29013.1 is 76%) all contain a glutamic acid at the equivalent of position E211 in the *E. coli* sequence, when aligned using Cobalt, and would therefore be predicted to demonstrate the desired activity if the glutamic acid were converted to serine.

Structural homology can also be used to identify amino acids in the active site of the TA enzyme that serve a similar coordination role as E211 does in the *E. coli* gabT enzyme and would therefore be predicted to confer a similar shift in substrate specificity when mutated. Phylogenetically distinct collections of TA enzymes can be screened to identify those that efficiently catalyze the desired reaction (conversion of PPO to L-glufosinate) and less efficiently catalyze the undesired reaction (accepting the conversion product as a substrate, for example, SSA). Therefore, TA enzymes having a serine at the equivalent position of E211 when aligned with the *E. coli* gab T TA (SEQ ID NO:6) may be used in the methods described herein. It may also be useful to use various enzyme improvement techniques well known in the art to further improve the desired activity, reduce the undesirable activity, or both.

Additional methods to reduce the levels of KG include non-enzymatic oxidation by various means, such as hydrogen peroxide, reduction, either enzymatic or non-enzymatic, and degradation catalyzed by an ethylene synthetase. In CN107119084A, a method is described to reduce KG using an ethylene synthase, which catalyzes the conversion of 3 KG, 3 $O_2$, and 1 arginine to 2 ethylene, 1 succinate, 1 guanidine, 1 pyrroline-5-carboxylate, 7 carbon dioxide, and 3 $H_2O$. While the use of an ethylene synthetase can reduce the effective amount of KG, it requires the addition of several co-substrates and produces a number of products that must be removed from the reaction mass.

A higher yield of L-glufosinate can also be achieved by the enzymatic decarboxylation of α-ketoglutarate to succinate (succinic acid) by alpha-ketoglutarate dependent dioxygenases. These iron-containing enzymes catalyze a wide range of oxygenation reactions using oxygen and α-ketoglutarate as co-substrates. Many of these enzymes also require ascorbate (vitamin C) as reducing agent.

Taurine dioxygenase (EC 1.14.11.17) is one such enzyme, which converts α-ketoglutarate to succinate and carbon dioxide, while also converting taurine and oxygen to sulfite and aminoacetaldehyde. Xanthine dioxygenase (EC 1.14.11.48) is another such enzyme, which converts α-ketoglutarate to succinate and carbon dioxide, while also converting xanthine and oxygen to urate.

With these dioxygenase enzymes, α-ketoglutarate is converted to succinate (succinic acid) which, unlike the succinic semialdehyde produced by KGDs, is not a substrate of any other enzyme in the process.

If amine donors other than glutamate or L-glutamate are used, the by-product can be reduced in amount using various additional methods. Those already known in the art include spontaneous decarboxylation of oxaloacetate (a by-product if aspartate is the amine donor) as described in U.S. Pat. No. 6,936,444 and, although not utilized to produce L-glufosinate, decarboxylation of pyruvate (a by-product if alanine is the amine donor) as described in U.S. Pat. No. 9,074,228. If certain amine donors other than glutamate or L-glutamate are used, decarboxylases can also be used to reduce the by-products. For example, branched-chain ketoacid decarboxylase can be used to decarboxy late 2-oxobutanoic acid, the by-product if 2-aminobutyric acid is the amine donor and alpha ketoisovaleric acid, the by-product if valine is the amine donor (Gocke, D., Nguyen, C. L., Pohl, M., Stillger, T., Walter, L. & Müller, M., Advanced Synthesis & Catalysis 2007, 349, 1425-1435). Other methods to reduce the amount of the by-product include reduction or oxidation of the carboxylic acid, aldehyde, or ketone, using either chemical or enzymatic means, for example, glycolaldehyde dehydrogenase can be used to catalyze the reduction of glycolaldehyde, the by-product if ethanolamine is the amine donor.

The effective levels of KG exposed to the TA enzyme could also be reduced by sequestering KG from the TA enzyme, and, optionally, the rest of the reaction mass. In one embodiment, a solid substrate with affinity for KG is present or added to the reaction vessel. This could include ion exchange resin, affinity resin, size exclusion resin, or other resin or substrate. In another embodiment, the reaction mass is removed from the presence of the TA enzyme and exposed to the solid substrate. For example, the reaction mass could be filtered from the main reaction vessel and applied to a resin that preferentially bound KG. The reaction mass containing reduced amounts of KG could be then re-exposed to the TA enzyme. Single, repeated, or continuous removal of KG from the reaction mass could shift the equilibrium of the reaction catalyzed by the TA enzyme toward L-glufosinate.

Several DAAO enzymes are known in the art and can be used in the methods described herein, as long as they are capable of accepting D-glufosinate as a substrate and provide an activity sufficient to level to drive the reaction. The DAAO enzymes useful in the methods described herein have an activity of equal to or greater than about 3 μmol/min*mg, greater than about 4 μmol/min*mg, or higher. A wild type enzyme can be used in the methods described herein as long as the enzyme has an activity level as set forth above. Such DAAO enzymes that can be used in the method include those from Rhodosporidium toruloides, Trigonopsis *variabilis, Fusarium* sp, *Candida* sp, Schizosasaccharomyces sp, *Verticillium* sp. Neolentinus lepideus. *Trichoderma reesei. Trichosporon* oleaginosus, and the like that have been modified to increase activity. Any DAAO enzyme can be used as a starting enzyme including those having sequences corresponding to Swissprot accession numbers P80324, Q99042, P00371, and P24552 or SPTREMBL numbers Q9HGY3 and Q9Y7N4 or GenBank numbers KZT28066.1, XP_006968548.1, and KLT40252.1. The DNA sequences which encode the DAAO may be selected from sequences set forth in EMBL accessions A56901, RGU60066, Z50019, SSDA04, D00809, AB042032, RCDAAOX, A81420, and SPCC1450, or may be codon optimized from the protein sequences indicated above for optimal expression in the chosen expression host(s). U.S. Pat. No. 8,227,228 describes DAAO enzymes from *Candida intermedia*. Such sequences are herein incorporated by reference. These enzymes can be modified for increased activity and used in the methods described herein.

Additional DAAO enzymes can be identified in a variety of ways, including sequence similarity and functional screens. The DAAO enzyme may be a mutant DAAO enzyme that is capable of accepting D-glufosinate as a substrate. In Hawkes et al., supra, a mutant DAAO based on the sequence from Rhodosporidium toruloides (consisting of the F58K and M213S mutations) has been shown to accept D-glufosinate as a substrate (Hawkes et al. (2011) Plant Biotechnol J. 9 (3): 301-14). Other DAAO enzymes can be similarly modified to accept D-glufosinate and have greater activity, i.e., the activity needed to drive the methods described herein. In the same manner, known DAAO enzymes may be improved by mutagenesis, and/or novel DAAO enzymes could be identified.

In some embodiments, mutant enzymes can be made and tested in the methods described herein. Mutant DAAO enzymes (e.g., from *Rhodotorula gracilis*) can include one mutation, two mutations, three mutations, or more than three mutations (e.g., four mutations, five mutations, six mutations, seven mutations, eight mutations, nine mutations, or ten mutations or more) at positions in the mutant sequence as compared to the wild type sequence. The mutant DAAO can optionally comprise mutations at positions 54, 56, 58, 213, and/or 238. In some embodiments, such mutants can comprise amino acid substitutions at positions 54 and 56 when compared with the wild type sequence. In other embodiments, such mutants can comprise amino acid substitutions at positions 54 and 58 when compared to the wild type sequence. In other embodiments, such mutants can include amino acid substitutions at positions 54, 213, and 238 when compared with the wild type sequence. In other embodiments, such mutants can include amino acid substitutions at positions 54, 56, 58, and 213 when compared with the wild type sequence.

Optionally, at position 54, the wild type asparagine may be replaced by Ala, Cys, Gly, Ile, Ser, Leu, or, more preferably, Thr or Val. For example, the mutant DAAO can comprise one of the following mutations at position 54: N54C, N54L, N54T, or N54V.

Optionally, at position 56, the wild type threonine can be replaced by Ala, Cys, Gly, Ile, Asn, Arg, Ser, Thr, Met, or Val. See, U.S. Pat. No. 7,939,709, which is incorporated herein by reference. For example, the mutant DAAO can comprise the T56M or the T56N mutation.

Additionally, at position 58, the wild type Phe can be replaced by Lys, Arg, Gln, Thr, Gly, Ser, Ala, Arg, Asn, or His. The mutant DAAO can optionally comprise one of the following mutations at position 58: F58A, F58G, F58H, F58K, F58N, F58Q, F58R, F58S, or F58T. In some embodiments, the mutant DAAO does not include a mutation at position 58.

Optionally, at position 213, the wild type methionine is replaced by Arg, Lys, Ser, Cys, Asn, or Ala. In some examples, the mutant DAAO can comprise the mutation M213S.

Optionally, at position 238, the wild type tyrosine is replaced by His, Ser, Cys, Asn, or Ala.

In some embodiments, the mutant DAAO can comprise one or more of the following combinations of mutations: F58K and M213S: N54T and T56M: N54V and F58Q: N54C and F58H: N54T and F58T: N54T and F58G: N54T and F58Q: N54T and F58A: N54L and F58R: N54V and F58R: N54V and F58N: N54V, T56N, F58H, and M213S; and/or N54V, F58Q, and M213S.

In one embodiment, the mutant DAAO comprises mutations in other DAAO enzymes in positions equivalent to positions 54, 56, 58, 213, and/or 238 of Rhodosporidium toruloides DAAO or Trigonopsis *variabilis* DAAO.

Other suitable D amino acid oxidases may be obtained preferably from fungal sources. Such DAAO enzymes can be identified and tested for use in the methods described herein. To determine if the enzyme will accept D-glufosinate as a substrate, an oxygen electrode assay (Hawkes, 2011, supra), colorimetric assay (Berneman A, Alves-Ferreira M, Coatnoan N, Chamond N, Minoprio P (2010) Medium/High Throughput D-Amino Acid Oxidase Colorimetric Method for Determination of D-Amino Acids. Application for Amino Acid Racemases. J Microbial Biochem Technol 2:139-146), and/or direct measurement (via high performance liquid chromatography (HPLC), liquid chromatography mass spectrometry (LC-MS), or similar) of product formation can be employed.

The reaction catalyzed by the DAAO enzyme requires oxygen. Therefore, in one embodiment, aeration is a component of the DAAO reaction step. In some embodiments, oxygen, oxygen enriched air, an oxygen enriched gas stream, or air, is introduced to the reaction, either in the head space or by sparging gas through the reaction vessel, intermittently or continuously, to enhance the rate of reaction. Additionally, in other embodiments, optionally combined with sparging gas through the reaction vessel, a pressurized reactor may be used. That is, the reactor may be sealed and allowed to consume $O_2$. Using a sealed chamber would limit vapor emissions.

When a DAAO enzyme catalyzes the conversion of D-glufosinate to PPO, hydrogen peroxide ($H_2O_2$) evolves. This may be damaging to enzymes and other components of the biotransformation (e.g., products and/or substrates). Therefore, in one embodiment, an enzyme, such as catalase, can be used in addition to the DAAO enzyme to catalyze the elimination of hydrogen peroxide.

In some embodiments, hydrogen peroxide can be eliminated using catalyzed and non-catalyzed decomposition reactions. For example, hydrogen peroxide can be eliminated by a non-catalyzed decomposition reaction using increased heat and/or pH. Hydrogen peroxide can also be eliminated by a catalyzed decomposition reaction using, for example, transition metals and other agents, such as potassium iodide. In addition to eliminating hydrogen peroxide, the use of catalase also produces oxygen ($O_2$). The production of oxygen by catalase can aid in facilitating the conversion of D-glufosinate to PPO using the DAAO enzyme, as DAAO requires oxygen to function.

Other enzymes can be used to catalyze the conversion of D-glufosinate to PPO. For example, a DAAD enzyme that accepts D-glufosinate as a substrate can be used. It is recognized that in methods where a DAAD is used, the DAAD catalyzed reaction can include redox cofactor recycling. This involves oxidizing the reduced acceptor so that it can accept more electrons from D-glufosinate.

In one embodiment, chemical oxidative deamination, wherein an intermediate α-ketoacid is produced from the parent amino acid, can be used in the methods described herein to convert D-glufosinate to L-glufosinate. Chemical oxidative deamination involves the conversion of an amine group to a keto group with concomitant release of ammonia typically using metal ions such as those of copper or cobalt in an aqueous solution at temperatures between room temperature and the boiling point of the solution and at a pH in the range of about 4-about 10. See, for example, Ikawa and Snell (1954) J. Am. Chem. Soc. 76 (19): 4900-4902, herein incorporated by reference.

The substantially complete (greater than 70%, greater than 75%, greater than 80%, greater than 85%, greater than 90%, or greater than 95%) conversion of D-glufosinate to PPO can occur within 24 hours, within 18 hours, within 12 hours, within 8 hours, or less.

The second step of the method described herein involves the conversion of PPO to L-glufosinate using a transaminase (TA) enzyme. A TA with the required stereospecificity that accepts PPO as a substrate catalyzes the amination of PPO to L-glufosinate.

If the reaction is conducted as a two stage process where the D-glufosinate is substantially converted to PPO in the absence of amine donor and/or transaminase, starting amounts of PPO in the second stage typically range from 10 g/L to 140 g/L: 20 g/L to 140 g/L: or from 30 g/L to 140 g/L. If the reaction is conducted in a single stage process, the starting amounts of PPO are typically less than 1 g/L and the highest levels of PPO during the reaction are typically less than 25 g/L. The amine donor is initially present at between 1 and 50 fold molar excess over the starting amount of racemic glufosinate.

TAs useful in the methods described herein include the gabT transaminase from *Escherichia coli* (UniProt P22256), which has been shown to catalyze the desired reaction with PPO as a substrate (Bartsch et al. (1990) Appl Environ Microbiol. 56 (1): 7-12). Another enzyme has been evolved to catalyze the desired reaction at a higher rate using isopropylamine as an amine donor (Bhatia et al. (2004) Peptide Revolution: Genomics, Proteomics & Therapeutics, Proceedings of the Eighteenth American Peptide Symposium, Ed. Michael Chorev and Tomi K. Sawyer, Jul. 19-23, 2003, pp. 47-48). Additionally, TA enzymes from numerous microorganisms, such as *Streptomyces hygroscopicus, Streptomyces viridochromogenes, Candida albicans*, and others can be used in the practice of the methods described herein. In particular, see, for example, EP0249188, and U.S. Pat. No. 5,162,212, incorporated herein by reference. Where desired, the enzymes can be evolved by mutagenesis to increase their activities. Mutant TA enzymes can be selected for desired activity by the assays outlined in Schulz et al., Appl Environ Microbiol. (1990) Jan. 56 (1): 1-6, and/or by direct measurement of the products by HPLC, LC-MS, or similar products.

Additional TA enzymes for use in the methods can be identified by screening collections of TAs, such as those sold by Prozomix Limited (Northumberland, United Kingdom), SyncoZymes (Shanghai, China), Evocatal (Monheim am Rhein, Germany), Codexis (Redwood City, CA), or Abcam (Cambridge, United Kingdom) for the desired activity. Alternatively, sequence similarity can be used to identify novel TA enzymes. Finally, TA enzymes can also be identified from organisms capable of catalyzing the desired reaction.

The selection of an appropriate amine donor is important for an economical conversion of D-glufosinate to L-glufosinate. A variety of issues may be considered, including the cost of the donor, equilibrium thermodynamics, potential recovery of the donor, separation of the ketoacid product from the desired L-glufosinate, and others. Consequently, TA enzymes that accept several different amine donors can be used, including low cost amine donors such as L-aspartate or racemic aspartate, L-glutamate or racemic glutamate, L-alanine or racemic alanine, L-phenylethylamine or racemic phenylalanine, L-glycine or racemic glycine, L-lysine or racemic lysine, L-valine or racemic valine, L-serine or racemic serine, L-glutamine or racemic glutamine, isopropylamine, sec-buty lamine, ethanolamine, 2-aminobutyric acid, and diaminoproprionic acid. In some embodiments, the amine donor is not aspartate or aspartic acid (e.g., L-aspartic acid, D-aspartic acid, or racemic D,L-aspartic acid).

A wild type TA that accepts a desired amine donor can be identified, or a TA that does not normally accept a desired amine donor can be evolved to accept the desired substrate. Optionally, the transaminase is not an aspartate transaminase. Optionally, the transaminase is not 4-amino-butyrate: 2-ketoglutarate transaminase. In some embodiments, the transaminase is not a combination enzyme system that includes a PPT-specific transaminase and glutamate: oxaloacetate transaminase.

As indicated in a third step of the method to produce L-glufosinate, the alpha keto by-product produced is reduced driving the reaction to complete or substantially complete conversion of the PPO to L-glufosinate. As indicated, the means for reducing the by-product may vary depending on the amine donor.

Using the methods described herein, substantially complete conversion of PPO to L-glufosinate may occur within 48 hours, within 24 hours, within 12 hours, within 8 hours, or within 4 hours. Substantially complete, in this context, means that the conversion of PPO to L-glufosinate is greater than about 90%, greater than about 95%, greater than about 96%, greater than about 97%, greater than about 98%, greater than about 99%, or all detectable PPO is converted.

If the reaction occurs in a single container or vessel, the TA enzyme can be added with the DAAO enzyme or added at a later time, e.g., after the DAAO enzyme has been allowed to catalyze some or substantially all of the oxidative deamination.

Enzymes can be added to the reaction by a number of methods. One approach is to express the enzyme(s) in microorganism(s) such as *E. coli, S. cerevisiae. P. pastoris*, and others, and to add the whole cells to the reactions as whole cell biocatalysts. Another approach is to express the enzyme(s), lyse the microorganisms, and add the cell lysate. Yet another approach is to purify, or partially purify, the enzyme(s) from a lysate and add pure or partially pure enzyme(s) to the reaction. If multiple enzymes are required for a reaction, the enzymes can be expressed in one or several microorganisms, including expressing all enzymes within a single microorganism.

A further approach, which can be combined with the above approaches, is to immobilize enzyme(s) to a support (exemplary strategies are outlined in Datta et al. (2013) 3 Biotech. Feb: 3 (1): 1-9). Not intending to be limiting. enzymes, either singly or in combination, can, for example, be adsorbed to, or covalently or non-covalently attached to, or entrapped within, natural or synthetic polymers or inorganic supports, including aggregates of the enzyme(s) themselves. Once immobilized, the enzyme(s) and support can be dispersed into bulk solution or packed into beds, columns, or any number of similar approaches to interacting reaction solution with the enzymes. Since aeration is important for the DAAO reaction envisioned here, bubble columns or similar may be used for enzyme immobilization. As examples, reaction mixture can be flowed through a column of immobilized enzymes (flow reaction), added to a fixed bed or column of immobilized enzymes, allowed to react, and either removed from the bottom or top of the reaction vessel (plug flow), or added to dispersed immobilized enzymes and allowed to react then the immobilized enzymes removed by filtration, centrifugation, or similar (batch). Thus, any method for immobilization of the enzymes may be employed in the methods described herein.

The DAAO, TA, and/or other reactions can occur in a buffer. Exemplary buffers commonly used in biotransformation reactions include Tris, phosphate, or any of Good's buffers, such as 2-(N-morpholino) ethanesulfonic acid (MES): N-(2-Acetamido) iminodiacetic acid (ADA): piperazine-N,N'-bis(2-ethanesulfonic acid) (PIPES): N-(2-Acetamido)-2-aminoethanesulfonic acid (ACES): α-Hydroxy-4-morpholinepropanesulfonic acid (MOPSO); cholamine chloride: 3-(N-morpholino) propanesulfonic acid (MOPS): N,N-Bis (2-hydroxyethyl)-2-aminoethanesulfonic acid (BES): 2-[[1,3-dihydroxy-2-(hydroxy methyl) propan-2-yl]amino]ethanesulfonic acid (TES): 4-(2-hydroxyethyl)-1-piperazineethanesulfonic acid (HEPES): 3-(Bis (2-hydroxyethyl)amino)-2-hydroxypropane-1-sulfonic acid (DIPSO): acetamidoglycine, 3-(N-Tris (hydroxymethyl)methylamino (-2-hydroxypropanesulfonic acid (TAPSO): Piperazine-N, N'-bis(2-hydroxypropanesulfonic acid) (POPSO): 4-(2-Hydroxyethyl) piperazine-1-(2-hydroxypropanesulfonic acid) (HEPPSO): 3-[4-(2-Hydroxyethyl)-1-piperazinyl]propanesulfonic acid (HEPPS); tricine: glycinamide; bicine: or 3-[[1,3-dihydroxy-2-(hydroxymethyl) propan-2-yl]amino]propane-1-sulfonic acid (TAPS). Additional exemplary buffer recipes can be found in Whittall, J. and Sutton, P. W. (eds) (2012) Front Matter, in Practical Methods for Biocatalysis and Biotransformations 2, John Wiley & Sons, Ltd, Chichester, UK. In some embodiments, ammonium can act as a buffer. One or more organic solvents can also be added to the reaction.

Surprisingly, the DAAO, TA, and/or other reactions can occur with no or low levels (less than 1 mM) of buffer added (other than ammonium that may optionally be present due to addition of racemic glufosinate ammonium). In particular, immobilized DAAO, TA, and KGD enzymes may be stable and active in the presence of less than 1 mM phosphate buffer and with no other buffer except any ammonium present due to the addition of racemic glufosinate ammonium.

The racemic glufosinate starting material can be provided in a number of forms. Various salts of racemic glufosinate, such as ammonium and hydrochloride, or the zwitterion, can be used. The racemic glufosinate may be in the form of a solid powder (such as a powder of greater than 80%, 85%, 90%, or 95% purity) or an aqueous solution (such as a roughly 50% solution of racemic glufosinate).

In some embodiments, the reaction occurs within a defined pH range, which can be between pH 4 to pH 10 (e.g., between pH 6 and pH 9, such as approximately pH 7.5 to pH 8).

In some embodiments, the reaction occurs at a defined temperature. The temperature can be kept at a point between room temperature and the boiling point of the solvent, most typically between room temperature and 50° C.

Additional steps to further purify the L-glufosinate can be added. Such further purification and isolation methods include ion exchange, extraction, salt formation, crystallization and filtration: each may be used multiple times or in suitable combination. Enzymes can be removed by simple filtration if supported, or if free in solution by the use of ultrafiltration, the use of absorbants like celite, cellulose or carbon, or denaturation via various techniques known to those skilled in the art.

Ion exchange processes effect separation by selective adsorption of solutes onto resins chosen for this purpose. Because products and impurities must be dissolved in a single solution prior to adsorption, concentration of the purified product stream by evaporation or distillation prior to isolation is usually required. Examples of the use of ion exchange for purification are described by Schultz et al., EP0249188 (A2), U.S. Pat. No. 9,834,802, and International PCT Patent Application PCT/US2018/042503.

Purification may be achieved by the formation of an insoluble salt of L-glufosinate by the addition of a suitable acid, including hydrochloric acid, sulfuric acid, phosphoric acid, nitric acid, acetic acid and the like. Similarly, the purification may be achieved by the addition of a suitable base to form an insoluble salt. Useful bases include hydroxides, carbonates, sulfates and phosphates of alkali metals or hydroxides, carbonates, sulfates and phosphates of alkali earth metals. Other bases which contain nitrogen may be used, including ammonia, hydroxylamine, isopropylamine, triethylamine, tributylamine, pyridine, 2-picoline, 3-picoline, 4-picoline, 2,4-lutidine, 2,6-lutidine, morpholine, N-methymorpholine, 1,8-diazabicyclo[5.4.0]undec-7-ene, and dimethylethanolamine. It may be advantageous to concentrate the mixture or to add a solvent (or both) to maximize yield and optimize purity of the desired salt. Solvents suitable for this purpose include those in which the solubility of the desired salt is very low (such solvents are often called "anti-solvents"). Salts of L-glufosinate can be transformed into forms of glufosinate suitable for formulation by standard methods known to those skilled in the art. Alternatively, the L-glufosinate can be isolated as a zwitterion.

U.S. Pat. No. 9,255,115 B2 describes how the hydrochloric acid salt of L-glufosinate can be converted to the zwitterionic form with a base such as sodium hydroxide or sodium methoxide and then crystallized from aqueous alcohol solvent to afford L-glufosinate in relatively high purity. This method has the advantage of producing crystalline L-glufosinate that is not hygroscopic and therefore maintains a higher purity compared to amorphous L-glufosinate when exposed to humidity over time.

Other salts of L-glufosinate are known in the art. U.S. Pat. No. 5,767,309 and U.S. U.S. Pat. No. 5,869,668 teach the use of chiral alkaloid bases to form diastereomeric salts with racemic glufosinate. Purification is achieved because the salt of L-glufosinate precipitates from solution in much larger quantity than the corresponding salt of D-glufosinate. Therefore, this method could be used with the methods described herein to obtain L-glufosinate with high enantiomeric excess, if desired.

Optionally, purification may be achieved by first crystallizing one or more impurities, removing the impurities by filtration and then further purifying L-glufosinate from the resulting filtrate by forming a salt as previously described. This is advantageous if unreacted amine donor can be partially or completely isolated and used in subsequent reactions. Similarly, unreacted PPO that is partially or completely isolated may be recycled for use in subsequent reactions.

Extraction may be used to purify the product. DE 3920570 C2 describes a process in which excess glutamic acid (used as the amine donor) is precipitated by adjusting the solution pH to 3.7 to 4.2 with sulfuric acid. After filtering the glutamic acid, the filtrate pH is lowered to 1-2 whereupon other impurities are extracted into a solvent. After extraction and concentration, ammonia is added to the aqueous solution to a pH of 5-7 whereupon ammonium sulfate precipitates. The ammonium sulfate is removed by filtration and the resulting filtrate is concentrated to afford the ammonium salt of L-glufosinate.

Isolation of L-glufosinate or its salts may be desirable, for example, for the purpose of shipping solids to the location of formulation or use. Typical industrial methods of isolation may be used, for example, filtration, centrifugation, etc. Isolated product often requires the removal of water, volatile impurities and solvents (if present) and typical industrial drying equipment may be used for this purpose. Examples of such equipment include ovens, rotating drum dryers, agitated dryers, etc. In some cases, it may be advantageous to use a spray dryer.

It is not necessary to produce a solid product after purification. This may be advantageous if the formulation of L-glufosinate is to occur at the same site used for L-glufosinate production. L-glufosinate and many of its salts are readily soluble in water, and water is a convenient liquid to use for formulating products. For example, the amine donor is isolated by filtration and the resulting filtrate is concentrated by distillation. The pH of the filtrate may be adjusted to a desirable value and the resulting solution may be used as is or blended with formulation ingredients. In another example, a slurry of L-glufosinate or one of its salts may be prepared as described above and isolated by filtration. The solid could be dissolved directly on the filter by adding water or a suitable solvent to obtain a solution of L-glufosinate.

II. Compositions

Also described herein are compositions comprising the reaction products described above. In some embodiments, the composition substantially includes L-glufosinate and acceptable cationic or anionic salt forms such as the hydrochloride, ammonium, or isopropylammonium salts. In some embodiments, the composition comprises a mixture of L-glufosinate, PPO, and SSA. In some other embodiments, the compositions comprises a mixture of L-glufosinate and SSA.

The compositions described herein are useful for application to a field of crop plants for the prevention or control of weeds. The composition may be formulated as a liquid for spraying on a field. The L-glufosinate is provided in the composition in effective amounts. As used herein, effective amount means from about 10 grams active ingredient per hectare to about 1,500 grams active ingredient per hectare, e.g., from about 50 grams to about 400 grams or from about 100 grams to about 350 grams. In some embodiments, the active ingredient is L-glufosinate. For example, the amount of L-glufosinate in the composition can be about 10 grams, about 50 grams, about 100 grams, about 150 grams, about 200 grams, about 250 grams, about 300 grams, about 350) grams, about 400 grams, about 500 grams, about 550) grams, about 600 grams, about 650 grams, about 700 grams, about 750 grams, about 800 grams, about 850 grams, about 900 grams, about 950 grams, about 1,000 grams, about 1,050 grams, about 1,100 grams, about 1,150 grams, about 1,200 grams, about 1,250) grams, about 1,300 grams, about 1,350 grams, about 1,400 grams, about 1,450 grams, or about 1,500 grams L-glufosinate per hectare.

The herbicidal compositions (including concentrates which require dilution prior to application to the plants) described herein contain L-glufosinate (i.e., the active ingredient), optionally some residual D-glufosinate and/or PPO, and one or more adjuvant components in liquid or solid form.

The compositions are prepared by admixing the active ingredient with one or more adjuvants, such as diluents, extenders, carriers, surfactants, organic solvents, humectants, or conditioning agents, to provide a composition in the form of a finely-divided particulate solid, pellet, solution, dispersion, or emulsion. Thus, the active ingredient can be used with an adjuvant, such as a finely-divided solid, a liquid of organic origin, water, a wetting agent, a dispersing agent, an emulsifying agent, or any suitable combination of these. From the viewpoint of economy and convenience, water is the preferred diluent. However, not all the compounds are resistant to hydrolysis and in some cases this may dictate the use of non-aqueous solvent media, as understood by those of skill in the art.

Optionally, one or more additional components can be added to the composition to produce a formulated herbicidal composition. Such formulated compositions can include L-glufosinate, carriers (e.g., diluents and/or solvents), and other components. The formulated composition includes an effective amount of L-glufosinate. Optionally, the L-glufosinate can be present in the form of L-glufosinate ammonium. The L-glufosinate ammonium can be present in an amount ranging from 10% to 30% by weight of the formulated composition. For example, the L-glufosinate ammonium can be present in an amount of 10%, 12%, 14%, 16%, 18%, 20%, 22%, 24%, 26%, 28%, or 30% by weight of the formulated composition. Optionally, the L-glufosinate ammonium is present in an amount of 12.25% or of 24.5% by weight of the formulated composition.

In some examples, the formulated composition can include one or more surfactants. A suitable surfactant for use in the formulated composition includes sodium alkyl ether sulfate. The surfactant can be present in an amount from 10% to 40% by weight of the formulated composition. For example, the surfactant can be present in an amount of 10%, 12%, 14%, 16%, 18%, 20%, 22%, 24%, 26%, 28%, 30%, 32%, 34%, 36%, 38%, or 40% by weight of the formulated composition. Optionally, the sodium alkyl ether sulfate is present in an amount of 11.05%, 15.8%, 22.1%, or 31.6% by weight of the formulated composition.

The formulated composition can optionally include one or more solvents (e.g., organic solvents). Optionally, the solvent can be 1-methoxy-2-propanol, dipropylene glycol, ethylene glycol, propylene glycol, and mixtures thereof. The one or more solvents can be present in an amount ranging from 0.5% to 20% by weight of the formulated composition. For example, the total amount of solvents in the composition can be present in an amount of 0.5% to 18%, 5% to 15%, or 7.5% to 10% by weight of the formulated composition.

Optionally, the solvent includes a combination of two solvents. For example, the solvents in the formulation can include 1-methoxy-2-propanol and dipropylene glycol. The 1-methoxy-2-propanol can be present, for example, in an amount of 0.5% to 2% by weight of the formulated composition. For example, the 1-methoxy-2-propanol can be present in the amount of 0.5%, 0.6%, 0.7%, 0.8%, 0.9%, 1.0%, 1.1% 1.2%, 1.3%, 1.4%, 1.5%, 1.6%, 1.7%, 1.8%, 1.9%, or 2.0% by weight of the formulated composition. Optionally, the 1-methoxy-2-propanol is present in an amount of 0.5% or 1.0% by weight of the formulated composition. The dipropylene glycol can be present in an amount of from 4% to 18% by weight of the formulated composition. For example, the dipropylene glycol can be present in an amount of 4%, 6%, 8%, 10%, 12%, 14%, 16%, or 18% by weight of the formulated composition. Optionally, the dipropylene glycol is present in an amount of 4.3% or 8.6% by weight of the formulated composition.

The formulated composition can also include one or more polysaccharide humectants. Examples of suitable polysaccharide humectants include, for example, alkyl polysaccharides, pentoses, high fructose corn syrup, sorbitol, and molasses. The polysaccharide humectant, such as alkyl polysaccharide, can be present in the formulated composition in an amount ranging from 4% to 20% by weight of the formulated composition. For example, the total amount of polysaccharide humectant in the composition can be present in an amount of 4% to 18%, 4.5% to 15%, or 5% to 10% by weight of the formulated composition. In some examples, the total amount of polysaccharide humectant, such as the alkyl polysaccharide, present in the formulated composition can be 4%, 5%, 6%, 7%, 8%, 9%, 10%, 11%, 12%, 13%, 14%, 15%, 16%, 17%, or 18%. Optionally, the alkyl polysaccharide can be present in an amount of 3.2%, 4.9%, 6.2%, or 9.8% by weight of the formulated composition.

A diluent can also be included in the formulated composition. Suitable diluents include water and other aqueous components. Optionally, the diluents are present in an amount necessary to produce compositions ready for packaging or for use.

In one example, the formulated composition includes L-glufosinate ammonium in an amount of 12.25% by weight of the formulation: sodium alkyl ether sulfate in an amount of 31.6% by weight of the formulation: 1-methoxy-2-propanol in an amount of 1% by weight of the formulation; dipropylene glycol in an amount of 8.6% by weight of the formulation; and alkyl polysaccharide in an amount of 9.8% by weight of the formulation.

In another example, the formulated composition includes L-glufosinate ammonium in an amount of 24.5% by weight of the formulation: sodium alkyl ether sulfate in an amount of 31.6% by weight of the formulation: 1-methoxy-2-propanol in an amount of 1% by weight of the formulation: dipropylene glycol in an amount of 8.6% by weight of the formulation; and alkyl polysaccharide in an amount of 9.8% by weight of the formulation.

In another example, the formulated composition includes L-glufosinate ammonium in an amount of 12.25% by weight of the formulation: sodium alkyl ether sulfate in an amount of 15.8% by weight of the formulation: 1-methoxy-2-propanol in an amount of 0.5% by weight of the formulation: dipropylene glycol in an amount of 4.3% by weight of the formulation; and alkyl polysaccharide in an amount of 4.9% by weight of the formulation.

In another example, the formulated composition includes L-glufosinate ammonium in an amount of 24.5% by weight of the formulation: sodium alkyl ether sulfate in an amount of 22.1% by weight of the formulation: 1-methoxy-2-propanol in an amount of 1% by weight of the formulation; and alkyl polysaccharide in an amount of 6.2% by weight of the formulation.

In another example, the formulated composition includes L-glufosinate ammonium in an amount of 24.5% by weight of the formulation: sodium alkyl ether sulfate in an amount of 22.1% by weight of the formulation; propylene glycol in an amount of 15% by weight of the formulation; and alkyl polysaccharide in an amount of 6.2% by weight of the formulation.

In another example, the formulated composition includes L-glufosinate ammonium in an amount of 12.25% by weight of the formulation: sodium alkyl ether sulfate in an amount of 22.1% by weight of the formulation: 1-methoxy-2-propanol in an amount of 1% by weight of the formulation; and alkyl polysaccharide in an amount of 6.2% by weight of the formulation.

In another example, the formulated composition includes L-glufosinate ammonium in an amount of 12.25% by weight of the formulation: sodium alkyl ether sulfate in an amount of 11.05% by weight of the formulation: 1-methoxy-2-propanol in an amount of 0.5% by weight of the formulation; and alkyl polysaccharide in an amount of 3.1% by weight of the formulation.

Further components suitable for use in the formulated compositions provided herein are described in U.S. Pat. Nos. 4,692,181 and 5,258,358, both of which are incorporated by reference herein in their entireties.

The herbicidal compositions described herein, particularly liquids and soluble powders, can contain as further adjuvant components one or more surface-active agents in amounts sufficient to render a given composition readily dispersible in water or in oil. The incorporation of a surface-active agent into the compositions greatly enhances their efficacy. Surface-active agent, as used herein, includes wetting agents, dispersing agents, suspending agents, and emulsifying agents are included therein. Anionic, cationic, and non-ionic agents can be used with equal facility.

Suitable wetting agents include alkyl benzene and alkyl naphthalene sulfonates, sulfated fatty alcohols, amines or acid amides, long chain acid esters of sodium isothionate, esters of sodium sulfosuccinate, sulfated or sulfonated fatty acid esters petroleum solfonates, sulfonated vegetable oils, ditertiary acetylenic glycols, polyoxyethylene derivatives of alkylphenols (particularly isooctylphenol and nonylphenol), and polyoxethylene derivatives of the mono-higher fatty acid esters of hexitol anhydrides (e.g. sorbitan). Exemplary dispersants include methyl cellulose, polyvinyl alcohol, sodium lignin sulfonates, polymeric alkyl naphthalene sulfonates, sodium naphthalene sulfonate, polymethylene bisnaphthalenesulfonate, and sodium N-methyl-N-(long chain acid) laurates.

Water-dispersible powder compositions can be made containing one or more active ingredients, an inert solid extender, and one or more wetting and dispersing agents. The inert solid extenders are usually of mineral origin, such as the natural clays, diatomaceous earth, and synthetic minerals derived from silica and the like. Examples of such extenders include kaolinites, attapulgite clay, and synthetic magnesium silicate. Water-dispersible powders described herein can optionally contain from about 5 to about 95 parts by weight of active ingredient (e.g., from about 15 to 30 parts by weight of active ingredient), from about 0.25 to 25 parts by weight of wetting agent, from about 0.25 to 25 parts by weight of dispersant, and from 4.5 to about 94.5 parts by weight of inert solid extender, all parts being by weight of the total composition. Where required, from about 0.1 to 2.0 parts by weight of the solid inert extender can be replaced by a corrosion inhibitor or anti-foaming agent or both.

Aqueous suspensions can be prepared by dissolution or by mixing together and grinding an aqueous slurry of a water-insoluble active ingredient in the presence of a dispersing agent to obtain a concentrated slurry of very finely-divided particles. The resulting concentrated aqueous suspension is characterized by its extremely small particle size, so that when diluted and sprayed, coverage is very uniform.

Emulsifiable oils are usually solutions of active ingredient in water-immiscible or partially water-immiscible solvents together with a surface active agent. Suitable solvents for the active ingredient described herein include hydrocarbons and water-immiscible ethers, esters, or ketones. The emulsifiable oil compositions generally contain from about 5 to 95 parts active ingredient, about 1 to 50 parts surface active agent, and about 4 to 94 parts solvent, all parts being by weight based on the total weight of emulsifiable oil.

Compositions described herein can also contain other additaments, for example, fertilizers, phytotoxicants and plant growth regulants, pesticides, and the like used as adjuvants or in combination with any of the above-described adjuvants. The compositions described herein can also be admixed with the other materials, e.g., fertilizers, other phytotoxicants, etc., and applied in a single application.

In each of the formulation types described herein, e.g., liquid and solid formulations, the concentration of the active ingredients are the same.

It is recognized that the herbicidal compositions can be used in combination with other herbicides. The herbicidal compositions described herein are often applied in conjunction with one or more other herbicides to control a wider variety of undesirable vegetation. When used in conjunction with other herbicides, the presently claimed compounds can be formulated with the other herbicide or herbicides, tank mixed with the other herbicide or herbicides or applied sequentially with the other herbicide or herbicides. Some of the herbicides that can be employed in conjunction with the compounds described herein include: amide herbicides such as allidochlor, beflubutamid, benzadox, benzipram, bromobutide, cafenstrole, CDEA, chlorthiamid, cyprazole, dimethenamid, dimethenamid-P, diphenamid, epronaz, etnipromid, fentrazamide, flupoxam, fomesafen, halosafen, isocarbamid, isoxaben, napropamide, naptalam, pethoxamid, propyzamide, quinonamid and tebutam; anilide herbicides such as chloranocryl, cisanilide, clomeprop, cypromid, diflufenican, etobenzanid, fenasulam, flufenacet, flufenican, mefenacet, mefluidide, metamifop, monalide, naproanilide, pentanochlor, picolinafen and propanil: arylalanine herbicides such as benzoylprop, flamprop and flamprop-M: chloroacetanilide herbicides such as acetochlor, alachlor, butachlor, butenachlor, delachlor, diethatyl, dimethachlor, metazachlor, metolachlor. S-metolachlor, pretilachlor, propachlor, propisochlor, prynachlor, terbuchlor, thenylchlor and xylachlor: sulfonanilide herbicides such as benzofluor, perfluidone, pyrimisulfan and profluazol: sulfonamide herbicides such as asulam, carbasulam, fenasulam and oryzalin: antibiotic herbicides such as bilanafos: benzoic acid herbicides such as chloramben, dicamba, 2.3.6-TBA and tricamba: pyrimidiny loxy benzoic acid herbicides such as bispyribac and pyriminobac: pyrimidinylthiobenzoic acid herbicides such as pyrithiobac: phthalic acid herbicides such as chlorthal: picolinic acid herbicides such as aminopyralid, clopyralid and picloram: quinolinecarboxylic acid herbicides such as quinclorac and quinmerac: arsenical herbicides such as cacodylic acid. CMA. DSMA.

hexaflurate. MAA. MAMA, MSMA, potassium arsenite and sodium arsenite; benzoylcyclohexanedione herbicides such as mesotrione, sulcotrione, tefuryltrione and tembotrione: benzofuranyl alkylsulfonate herbicides such as benfuresate and ethofumesate; carbamate herbicides such as asulam, carboxazole chlorprocarb, dichlormate, fenasulam, karbutilate and terbucarb; carbanilate herbicides such as barban, BCPC, carbasulam.

carbetamide. CEPC, chlorbufam, chlorpropham. CPPC, desmedipham, phenisopham, phenmedipham, phenmedipham-ethyl, propham and swep: cyclohexene oxime herbicides such as alloxydim, butroxydim, clethodim, cloproxydim, cycloxydim, profoxydim, sethoxy dim, tepraloxydim and tralkoxydim: cyclopropylisoxazole herbicides such as isoxachlortole and isoxaflutole: dicarboximide herbicides such as benzfendizone, cinidon-ethyl, flumezin, flumiclorac, flumioxazin and flumipropyn: dinitroaniline herbicides such as benfluralin, butralin, dinitramine, ethalfluralin, fluchloralin, isopropalin, methalpropalin, nitralin, oryzalin, pendimethalin, prodiamine, profluralin and trifluralin: dinitrophenol herbicides such as dinofenate, dinoprop, dinosam, dinoseb, dinoterb. DNOC, etinofen and medinoterb: diphenyl ether herbicides such as ethoxyfen: nitrophenyl ether herbicides such as acifluorfen, aclonifen, bifenox, chlomethoxyfen, chlomitrofen, etnipromid, fluorodifen, fluoroglycofen, fluoronitrofen, fomesafen, furyloxyfen, halosafen, lactofen, nitrofen, nitrofluorfen and oxyfluorfen: dithiocarbamate herbicides such as dazomet and metam; halogenated aliphatic herbicides such as alorac, chloropon, dalapon, flupropanate, hexachloroacetone, iodomethane, methyl bromide, monochloroacetic acid. SMA and TCA; imidazolinone herbicides such as imazamethabenz, imazamox, imazapic, imazapyr, imazaquin and imazethapyr: inorganic herbicides such as ammonium sulfamate, borax, calcium chlorate, copper sulfate, ferrous sulfate, potassium azide, potassium cyanate, sodium azide, sodium chlorate and sulfuric acid: nitrile herbicides such as bromobonil, bromoxynil, chloroxynil, dichlobenil, iodobonil, ioxynil and pyraclonil: organophosphorus herbicides such as amiprofos-methyl, anilofos, bensulide, bilanafos, butamifos, 2,4-DEP, DMPA, EBEP, fosamine, glyphosate and piperophos: phenoxy herbicides such as bromofenoxim, clomeprop. 2.4-DEB, 2,4-DEP, difenopenten, disul, erbon, etnipromid, fenteracol and trifopsime; phenoxyacetic herbicides such as 4-CPA. 2,4-D, 3,4-DA. MCPA, MCPA-thioethyl and 2,4,5-T: phenoxy butyric herbicides such as 4-CPB, 2,4-DB, 3,4-DB, MCPB and 2,4,5-TB; phenoxypropionic herbicides such as cloprop, 4-CPP, dichlorprop, dichlorprop-P. 3,4-DP, fenoprop, mecoprop and mecoprop-P: ary loxyphenoxypropionic herbicides such as chlorazifop, clodinafop, clofop, cyhalofop, diclofop, fenoxaprop, fenoxaprop-P, fenthiaprop, fluazifop, fluazifop-P, haloxyfop, haloxyfop-P, isoxapyrifop, metamifop, propaquizafop, quizalofop, quizalofop-P and trifop: phenylenediamine herbicides such as dinitramine and prodiamine: pyrazolyl herbicides such as benzofenap, pyrazolynate, pyrasulfotole, pyrazoxyfen, pyroxasulfone and topramezone: pyrazolylphenyl herbicides such as fluazolate and pyraflufen: pyridazine herbicides such as credazine, pyridafol and pyridate: pyridazinone herbicides such as brompyrazon, chloridazon, dimidazon, flufenpyr, metflurazon, norflurazon, oxapyrazon and pydanon; pyridine herbicides such as aminopyralid, cliodinate, clopyralid, dithiopyr, fluroxypyr, haloxydine, picloram, picolinafen, pyriclor, thiazopyr and triclopyr: pyrimidinediamine herbicides such as iprymidam and tioclorim: quaternary ammonium herbicides such as cyperquat, diethamquat, difenzoquat, diquat, morfamquat and paraquat: thiocarbamate herbicides such as butylate, cycloate, di-allate, EPTC, esprocarb, ethiolate, isopolinate, methiobencarb, molinate, orbencarb, pebulate, prosulfocarb, pyributicarb, sulfallate, thiobencarb, tiocarbazil, tri-allate and vernolate: thiocarbonate herbicides such as dimexano, EXD and proxan: thiourea herbicides such as methiuron; triazine herbicides such as dipropetryn, triaziflam and trihydroxytriazine: chlorotriazine herbicides such as atrazine, chlorazine, cyanazine, cyprazine, eglinazine, ipazine, mesoprazine, procyazine, proglinazine, propazine, sebuthylazine, simazine, terbuthylazine and trietazine: methoxytriazine herbicides such as atraton, methometon, prometon, secbumeton, simeton and terbumeton: methylthiotriazine herbicides such as ametryn, aziprotryne, cyanatryn, desmetryn, dimethametryn, methoprotryne, prometryn, simetryn and terbutryn: triazinone herbicides such as ametridione, amibuzin, hexazinone, isomethiozin, metamitron and metribuzin; triazole herbicides such as amitrole, cafenstrole, epronaz and flupoxam: triazolone herbicides such as amicarbazone, bencarbazone, carfentrazone, flucarbazone, propoxycarbazone, sulfentrazone and thiencarbazone-methyl; triazolopyrimidine herbicides such as cloransulam, diclosulam, florasulam, flumetsulam, metosulam, penoxsulam and pyroxsulam: uracil herbicides such as butafenacil, bromacil, flupropacil, isocil, lenacil and terbacil: 3-phenyluracils: urea herbicides such as benzthiazuron, cumyluron, cycluron, dichloralurea, diflufenzopyr, isonoruron, isouron, methabenzthiazuron, monisouron and noruron: phenylurea herbicides such as anisuron, buturon, chlorbromuron, chloreturon, chlorotoluron, chloroxuron, daimuron, difenoxuron, dimefuron, diuron, fenuron, fluometuron, fluothiuron, isoproturon, linuron, methiuron, methyldymron, metobenzuron, metobromuron, metoxuron, monolinuron, monuron, neburon, parafluron, phenobenzuron, siduron, tetrafluron and thidiazuron: pyrimidinylsulfonylurea herbicides such as amidosulfuron, azimsulfuron, bensulfuron, chlorimuron, cyclosulfamuron, ethoxysulfuron, flazasulfuron, flucetosulfuron, flupyrsulfuron, foramsulfuron, halosulfuron, imazosulfuron, mesosulfuron, nicosulfuron, orthosulfamuron, oxasulfuron, primisulfuron, pyrazosulfuron, rimsulfuron, sulfometuron, sulfosulfuron and trifloxysulfuron; triazinylsulfonylurea herbicides such as chlorsulfuron, cinosulfuron, ethametsulfuron, iodosulfuron, metsulfuron, prosulfuron, thifensulfuron, triasulfuron, tribenuron, triflusulfuron and tritosulfuron: thiadiazolylurea herbicides such as buthiuron, ethidimuron, tebuthiuron, thiazafluron and thidiazuron; and unclassified herbicides such as acrolein, allyl alcohol, aminocyclopyrachlor, azafenidin, benazolin, bentazone, benzobicyclon, buthidazole, calcium cyanamide, cambendichlor, chlorfenac, chlorfenprop, chlorflurazole, chlorflurenol, cinmethylin, clomazone, CPMF, cresol, ortho-dichlorobenzene, dimepiperate, endothal, fluoromidine, fluridone, flurochloridone, flurtamone, fluthiacet, indanofan, methazole, methyl isothiocyanate, nipyraclofen, OCH, oxadiargyl, oxadiazon, oxaziclomefone, pentachlorophenol, pentoxazone, phenylmercury acetate, pinoxaden, prosulfalin, pyribenzoxim, pyriftalid, quinoclamine, rhodethanil, sulglycapin, thidiazimin, tridiphane, trimeturon, tripropindan and tritac. The herbicidal compositions described herein can, further, be used in conjunction with glyphosate or 2,4-D on glyphosate-tolerant or 2,4-D-tolerant crops. It is generally preferred to use the compositions described herein in combination with herbicides that are selective for the crop being treated and which complement the spectrum of weeds controlled by these compositions at the application rate employed. It is further generally preferred to apply the compositions described herein and other complementary herbicides at the same time, either as a combination formulation or as a tank mix.

III. Methods of Use of L-Glufosinate Compositions

The compositions described herein can be used in methods for selectively controlling weeds in a field or any other area, including, for example, a railway, lawn, golf course, and others where the control of weeds is desired. Optionally, the field or other area can contain a crop of planted seeds or crops that are resistant to glufosinate. The methods can include applying an effective amount of a composition comprising L-glufosinate as described herein to the field.

The compositions described herein are useful for application to a field of crop plants for the prevention or control of weeds. The composition may be formulated as a liquid for spraying on a field. The L-glufosinate is provided in the composition in effective amounts. As used herein, effective amount means from about 10 grams active ingredient per hectare to about 1,500 grams active ingredient per hectare, e.g., from about 50 grams to about 400 grams or from about 100 grams to about 350 grams. In some embodiments, the active ingredient is L-glufosinate. For example, the amount of L-glufosinate in the composition can be about 10 grams, about 50 grams, about 100 grams, about 150 grams, about 200 grams, about 250 grams, about 300 grams, about 350 grams, about 400 grams, about 500 grams, about 550 grams, about 600 grams, about 650 grams, about 700 grams, about 750 grams, about 800 grams, about 850 grams, about 900 grams, about 950 grams, about 1,000 grams, about 1,050 grams, about 1,100 grams, about 1,150 grams, about 1,200 grams, about 1,250 grams, about 1,300 grams, about 1,350 grams, about 1,400 grams, about 1,450 grams, or about 1,500 grams L-glufosinate per hectare.

IV. Exemplary Embodiments

Non-limiting embodiments include:

1. A method for making L-glufosinate, comprising: reacting D-glufosinate with a D-amino acid oxidase (DAAO) enzyme to form PPO (2-oxo-4-(hydroxy (methyl) phosphinoyl) butyric acid) while aerating in an oxidation step: aminating the PPO by a transaminase (TA) enzyme, using an amine group from one or more amine donors to form L-glufosinate and an alpha ketoacid by-product or ketone by-product in an amination step; and reducing an amount of the alpha ketoacid by-product or ketone by-product in a reduction step, wherein more than 90% of the PPO is converted to L-glufosinate.

2. The method of embodiment 1, wherein more than 91% of the PPO is converted to L-glufosinate.

3. The method of embodiment 1, wherein more than 92% of the PPO is converted to L-glufosinate.

4. The method of embodiment 1, wherein more than 93% of the PPO is converted to L-glufosinate.

5. The method of embodiment 1, wherein more than 94% of the PPO is converted to L-glufosinate.

6. The method of embodiment 1, wherein more than 95% of the PPO is converted to L-glufosinate.

7. The method of embodiment 1, wherein more than 96% of the PPO is converted to L-glufosinate.

8. The method of embodiment 1, wherein more than 97% of the PPO is converted to L-glufosinate.

9 The method of embodiment 1, wherein more than 98% of the PPO is converted to L-glufosinate.

10. The method of embodiment 1, wherein more than 99% of the PPO is converted to L-glufosinate.

11. The method of embodiment 1, wherein the DAAO enzyme is a mutant DAAO comprising one or more mutations at positions 54, 56, 58, 213, and 238, using SEQ ID NO:8 as a reference sequence, wherein the mutation at position 54 is selected from the group consisting of N54C, N54L, N54T, and N54V; the mutation at position 56 is T56M or T56N; and the mutation at position 58 is selected from the group consisting of F58A, F58G, F58H, F58K, F58N, F58Q, F58R, F58S, and F58T.

12. The method of embodiment 11, wherein the mutations comprise N54V, T56N, F58H, and M213S.

13. The method of embodiment 1, wherein the alpha ketoacid by-product is reduced by enzymatic conversion.

14. The method of any one of embodiments 1-13, wherein the TA enzyme is an enzyme encoded by SEQ ID NO:6 or SEQ ID NO: 7.

15. The method of any one of embodiments 1-13, wherein the TA enzyme is a GabT transaminase having the amino acid sequence set forth in SEQ ID NO:6 or SEQ ID NO:7.

16. The method of any one of embodiments 1-15, wherein the amine donor is glutamate or L-glutamate.

17. The method of embodiment 16, wherein the alpha ketoacid by-product is reduced in amount by the addition of a ketoglutarate decarboxylase (KGD) enzyme.

18. The method of any one of embodiments 1-17, wherein the oxidation, the amination, and the reduction steps are performed in a single container.

19. The method of any one of embodiments 1-17, wherein all reagents are substantially added at the start of the reaction.

20. The method of embodiment 18, wherein the reagents for the oxidation, the amination, and the reduction steps are added to the single container at different times.

21. The method of any one of embodiments 1-17, wherein the oxidation, the amination, and the reduction steps are performed in separate containers.

22. The method of any one of embodiments 1-17, wherein one or more of the enzymes are immobilized.

23. The method of any one of embodiments 1-17, wherein the by-product is sequestered from the reaction by binding or further conversion to another product.

24. A method for converting PPO to L-glufosinate comprising aminating the PPO by a transaminase (TA) enzyme, using an amine group from one or more amine donors to form L-glufosinate and an alpha ketoacid or ketone by-product, and reducing the amount of the alpha ketoacid or the ketone by-product wherein more than 90% of the PPO is converted to L-glufosinate.

25. The method of embodiment 24, wherein the alpha ketoacid or the ketone by-product is reduced in amount by the addition of an enzyme which reacts with the by-product.

26. The method of embodiment 25, wherein the amine donor is L-glutamate.

27. The method of embodiment 25, wherein the enzyme which reacts with the by-product is KGD.

28. The method of embodiment 27, wherein the KGD comprises the one of the sequences set forth in SEQ ID NO: 1 to 5.

29. The method of embodiment 24, wherein the TA enzyme is an enzyme encoded by SEQ ID NO:6 or SEQ ID NO:7.

30. The method of embodiment 24, wherein the TA enzyme is a GabT transaminase having the amino acid sequence set forth in SEQ ID NO:6 or SEQ ID NO: 7.

31. The method of embodiment 24, wherein the TA enzyme has lower affinity for SSA than for PPO.

32. A composition comprising L-glufosinate and succinic semialdehyde (SSA).

33. A composition comprising L-glufosinate ammonium in an amount from 10-30% by weight of the composition; one or more additional components selected from the group consisting of sodium alkyl ether sulfate in an amount from 10-40% by weight of the composition: 1-methoxy-2-propanol in an amount from 0.5-2% by weight of the composition; dipropylene glycol in an amount from 4-18% by weight of the composition; and alkyl polysaccharide in an amount from 4-20% by weight of the composition.

34. A composition comprising L-glufosinate ammonium in an amount from 10-30% by weight of the composition; one or more additional components selected from the group consisting of sodium alkyl ether sulfate in an amount from 10-40% by weight of the composition; propylene glycol in an amount from 5-20% by weight of the composition; and alkyl polysaccharide in an amount from 4-20% by weight of the composition.

35. A method for selectively controlling weeds in an area comprising: applying an effective amount of a composition comprising L-glufosinate at an enantiomeric excess of greater than 99% over D-glufosinate to the area.

36. A composition comprising L-glufosinate, PPO, and SSA, wherein the PPO is present in an amount less than 10% of the amount of L-glufosinate and SSA is present at a molar amount up to 2 times the amount of L-glufosinate.

37. A composition comprising greater than 90% L-glufosinate, less than 10% PPO, less than 10% of the alpha ketoacid or ketone by-product, and at least 25% of the conversion product relative to the amount of L-glufosinate.

The following examples are offered by way of illustration and not by way of limitation.

EXAMPLES

Example 1: Activity of Selected KGD Enzymes Utilizing KG as a Substrate

In this example, various KGD enzymes are tested for the activity of degrading KG into SSA. The following reactants were added at the start of the 470 uL reaction: 15 mM KG, 107 uM thiamine pyrophosphate (TPP), 4.5 mM MgCl2-6H$_2$O, 63 to 197 µg/mL KGD enzyme, 30 mM Kphos (pH 8). Reactions were incubated at 30° C. with 300 rpm shaking for 21 hours, and then left on the bench for 5 hours before HPLC analysis. The degradation of KG over time is shown in Table 1 after normalization of starting KG concentrations.

TABLE 1

| Time (hours) | M. smegmatis | S. apiospermum | M. maritypicum | A. enclensis | K. phytohabitans |
|---|---|---|---|---|---|
| 0 | 15.0 | 15.0 | 15.0 | 15.0 | 15.0 |
| 2 | 11.9 | 13.8 | 6.8 | 8.7 | 9.5 |
| 4 | 9.4 | 13.3 | 1.7 | 4.3 | 5.3 |
| 26 | 0.7 | 3.9 | 1.0 | 1.2 | 1.0 |

Example 2: Activity of Selected KGD Enzymes Utilizing PPO as a Substrate

In this example, various KGD enzymes are tested for the activity of decarboxylating PPO. The following reactants were added at the start of the 500 uL reaction: 40 mM PPO, 40 mM L-glufosinate, 0.1 mM thiamine pyrophosphate (TPP), 4.2 mM MgCl2-6H$_2$O, ~30-90 ug/mL KGD enzyme. Reactions were incubated at 30° C. with 300 rpm shaking for 4 hours. Reactions were then left on the bench for 71 hours, at which point an end point sample was taken. The normalized degradation of PPO over time is shown in Table 2.

TABLE 2

| Time (hours) | M. smegmatis | S. apiospermum | M. maritypicum | A. enclensis | K. phytohabitans |
| --- | --- | --- | --- | --- | --- |
| 0 | 40.0 | 40.0 | 40.0 | 40.0 | 40.0 |
| 2 | 40.5 | 39.4 | 45.0 | 42.2 | 40.1 |
| 4 | 40.3 | 36.0 | 40.8 | 35.0 | 39.8 |
| 75 | 42.4 | 34.8 | 38.3 | 35.4 | 38.5 |

Example 3: Activity of wild type and mutant TA enzymes in the L-glufosinate reaction In this example, wild type E. coli gabT TA enzyme and its E211S variant were tested for activity on the desired reaction of converting PPO and glutamate to KG and L-glufosinate. The following reactants were added at the start of the 500 uL reaction: 25 mM PPO, 25 mM L-glufosinate, 180 mM L-glutamate (3.6X molar excess of PPO+Glu-L), 0.2 mM PLP, 25 mM Kphos (pH 8.0) to bring to pH ~7.5, 75 µg/mL gabT. Reactions were incubated at 30° C. with 300 rpm shaking and samples taken for HPLC analysis. The normalized appearance of KG over time is shown in Table 3.

TABLE 3

| Time (hours) | Wild type | E211S mutant |
| --- | --- | --- |
| 0.0 | 0.0 | 0.0 |
| 0.2 | 10.9 | 2.0 |
| 0.5 | 14.2 | 5.1 |
| 1.0 | 14.5 | 7.9 |
| 5.0 | 14.4 | 14.1 |
| 24.5 | 14.5 | 14.8 |

Example 4: Activity of Wild Type and Mutant TA Enzymes in their Native Reactions In this example, wild type E. coli gabT TA enzyme and its E211S variant were tested for activity on the native reaction of converting SSA and glutamate to KG and GABA. The following reactants were added at the start of the 500 uL reaction: 250 mM L-glutamate, 50 mM SSA, 0.2 mM PLP, 50 mM Kphos (pH 8.0) and 30 mM NaOH to bring to pH 7.5, 75 µg/mL gabT enzyme. Reactions were incubated at 30° C. with 300 rpm shaking and samples taken for HPLC analysis. The normalized appearance of KG over time is shown in Table 4.

TABLE 4

| Time (minutes) | Wild type | E211S mutant |
| --- | --- | --- |
| 0 | 0.0 | 0.0 |
| 10 | 12.4 | 0.0 |

TABLE 4-continued

| Time (minutes) | Wild type | E211S mutant |
| --- | --- | --- |
| 30 | 13.2 | 0.0 |
| 60 | 13.5 | 0.5 |
| 1200 | 15.5 | 4.9 |

Example 5: Improved Yield of L-Glufosinate with the Addition of KGD Enzyme

Figure 3A:
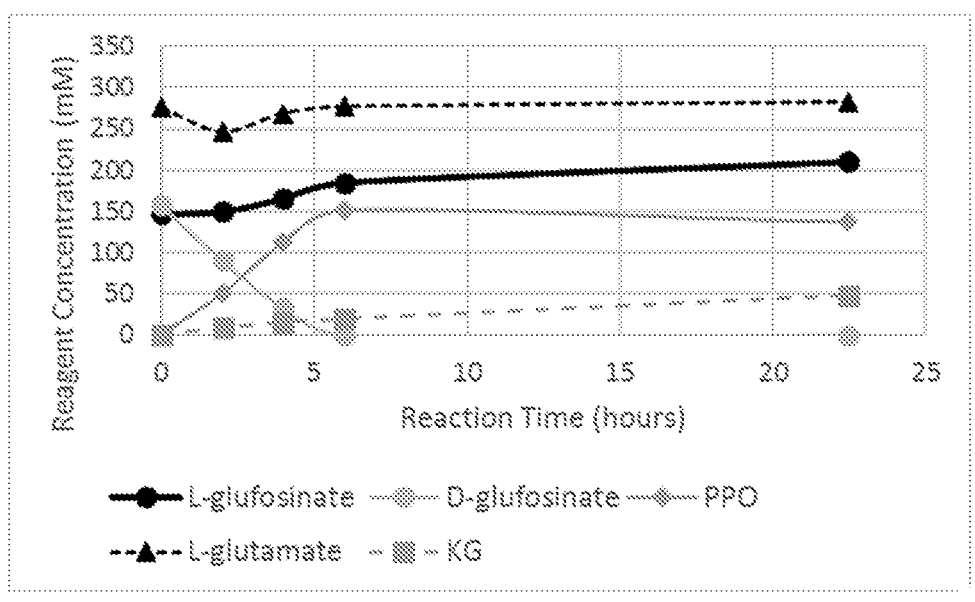
FIGS. 3A-C are graphs showing concentrations of L-glufosinate (black circles, black bold line), D-glufosinate (light grey circles, light grey solid line), PPO (dark grey diamonds, dark grey solid line), L-glutamate (black triangles, black dashed line), and KG (dark grey squares, dark grey dashed line) during a deracemization of racemic glufosinate utilizing a DAAO enzyme and a TA enzyme at two starting concentrations of L-glutamate without a KGD enzyme at 300 mM L-glutamate (FIG. 3A) and with a KGD enzyme at 300 mM L-glutamate (FIG. 3B) or 150 mM L-glutamate (FIG. 3C).
Figure 3B:
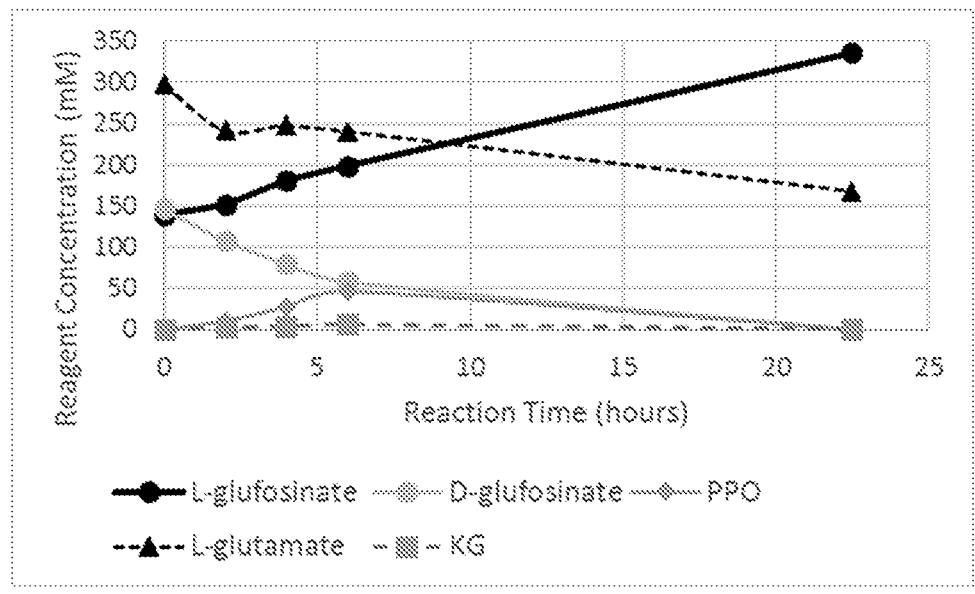
Figure 3C:
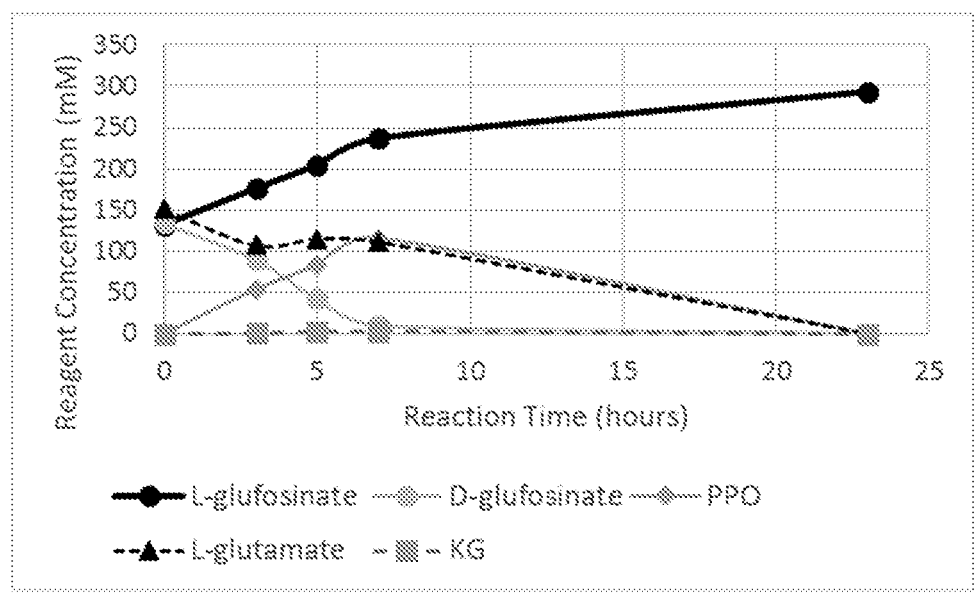

In this example, racemic glufosinate is deracemized using a DAAO enzyme, a TA enzyme, and with or without, a KGD enzyme. The following reactants were added at the start of the 500 uL reaction: 300 mM racemic glufosinate, 150 or 300 mM L-glutamate, 0.1 mM thiamine pyrophosphate (TPP), 4.2 mM MgCl2-6H$_2$O, 0.2 mM PLP, 0.2 mg/mL catalase lysate, 1 mg/mL DAAO (pure enzyme), 0.4 mg/mL E211S gabT (2.35 mg/mL CFE), +/−0.5 mg/mL KGD from A. enclensis (7.15 mg/mL CFE), and ~35 mM Kphos (pH 8) and 5 mM NaOH to adjust pH to ~7.5. Reactions were incubated open at 30° C. with 320 rpm shaking for the first 6 to 7 hours. Tubes were closed for overnight incubation to minimize evaporation. FIG. 3 shows the progress of the reaction without (A) or with (B and C) the addition of the KGD enzyme and a starting L-glutamate concentration of 300 mM (A and B) or 150 mM (C). In the graphs are shown the concentrations of L-glufosinate (black circles, black bold line), D-glufosinate (light grey circles, light grey solid line), PPO (dark grey diamonds, dark grey solid line), L-glutamate (black triangles, black dashed line), and KG (dark grey squares, dark grey dashed line).

Example 6: Improved Yield of L-Glufosinate with Mutant TA Enzyme

In this example, a mutant TA enzyme with reduced affinity for SSA as a substrate is used in a deracemization and the yield of L-glufosinate is higher than the wild type TA enzyme, even though the initial rate of production is higher for the wild type TA. The following reactants were added at the start of the 500 uL reaction: 300 mM D,L-Glufosinate, 150 mM L-Glutamate (MSG). 0.1 mM thiamine pyrophosphate (TPP), 4.2 mM MgCl2-6H$_2$O, 0.2 mM pyridoxal phosphate (PLP), 0.2 mg/mL catalase powder (Sigma), 1 mg/mL DAAO Ac302, 0.4 mg/mL TA (SEQ ID NO:6 is wild type, SEQ ID NO:7 is E211S mutant), 0.36 mg/mL A. enclensis KGD (SEQ ID NO:4), ~30 mM Kphos (pH 8), and 10 mM NaOH to adjust pH to 7.7. Reactions were incubated open at 30° C. with 320 rpm shaking for the first 4 hours. Tubes were closed for overnight incubation to minimize evaporation. The normalized amount of L-glufosinate (in millimolar) over time is shown in Table 5.

TABLE 5

| Time (hours) | Wild type | E211S mutant |
|---|---|---|
| 0 | 146 | 145 |
| 2 | 171 | 153 |
| 4 | 194 | 164 |
| 23 | 233 | 259 |

Example 7: Improved Yield of L-Glufosinate with the Addition of Various KGD Enzymes In this example, racemic glufosinate is deracemized using a DAAO enzyme, a TA enzyme, and with or without, various KGD enzymes. The following reactants were added at the start of the 500 uL reaction: 300 mM D,L-Glufosinate, 150 mM L-Glutamate (MSG). 0.1 mM thiamine pyrophosphate (TPP), 4.2 mM MgCl2-6H$_2$O, 0.2 mM pyridoxal phosphate (PLP), 0.2 mg/mL catalase powder (Sigma), 1 mg/mL DAAO Ac302, 0.4 mg/mL TA (E211S mutant), 0.5 mg/mL KGD (0.36 mg/mL for A. enclensis KGD, 0 mg/mL for No KGD), ~30 mM Kphos (pH 8), and 10 mM NaOH to adjust pH to 7.7. Reactions were incubated open at 30° C. with 320 rpm shaking for the first 4 hours. Tubes were closed for overnight incubation to minimize evaporation. The percent of PPO converted to L-glufosinate over time is shown in Table 6.

TABLE 6

| Time (hours) | No KGD | M. smegmatis SEQ ID NO: 1 | S. apiospermum SEQ ID NO: 2 | M. maritypicum SEQ ID NO: 3 | A. enclensis SEQ ID NO: 4 | K. phytohabitans SEQ ID NO: 5 |
|---|---|---|---|---|---|---|
| 0 | 0 | 0 | 0 | 0 | 0 | 0 |
| 2 | 14 | 16 | 49 | 41 | 17 | 45 |
| 4 | 12 | 31 | 63 | 48 | 22 | 48 |
| 23 | 22 | 85 | 96 | 97 | 87 | 94 |

Example 8: Activity of KGD Enzymes Immobilized on HA403 Resin

In this example, KG is decarboxylated using various immobilized KGD enzymes. The following reactants were added at the start of the 2.5 mL reaction: 100 mM KG, 0.17 mM TPP, 4 mM MgCl2-6H$_2$O, 2 mg/mL KGD immobilized on 0.25 g ReliZyme HA403 resin (Resindion), 100 mM Kphos (pH 7), 177.5 mM NaOH to pH 6.47 at 23° C. Reactions were incubated in closed 50 mL tubes at 30° C. with 275 rpm shaking. The concentration of KG over time is shown in Table 7.

TABLE 7

| Time (hours) | S. apiospermum SEQ ID NO: 2 | M. maritypicum SEQ ID NO: 3 | A. enclensis SEQ ID NO: 4 | K. phytohabitans SEQ ID NO: 5 |
|---|---|---|---|---|
| 0 | 95 | 98 | 90 | 94 |
| 4 | 79 | 45 | 57 | 48 |
| 21 | 34 | 0 | 7 | 0 |
| 27 | 34 | 0 | 3 | 0 |
| 43.5 | 29 | 0 | 0 | 0 |

Example 9: Activity of KGD Enzymes Immobilized on HA403 Resin

In this example, KG is decarboxylated using various immobilized KGD enzymes. The following reactants were added at the start of the 2.5 mL reaction: 100 mM KG, 0.1 mM TPP, 4 mM MgCl2-6H$_2$O, 1 mg/mL KGD immobilized on 0.5 g Lifetech ECR8209F (Purolite), 100 mM Kphos (pH 7), 170 mM NaOH to pH 6.5 at 2° C. Reactions were incubated in closed 50 mL tubes at 30° C. with 275 rpm shaking. The concentration of KG over time is shown in Table 8.

TABLE 8

| Time (hours) | M. smegmatis SEQ ID NO: 1 | S. apiospermum SEQ ID NO: 2 | M. maritypicum SEQ ID NO: 3 | A. enclensis SEQ ID NO: 4 | K. phytohabitans SEQ ID NO: 5 |
|---|---|---|---|---|---|
| 0 | 96 | 95 | 96 | 97 | 98 |
| 3 | 80 | 61 | 74 | 94 | 64 |
| 6 | 62 | 40 | 53 | 89 | 40 |
| 70 | 20 | 0 | 1 | 34 | 0 |

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. A method for making L-glufosinate, comprising:

reacting D-glufosinate with a D-amino acid oxidase (DAAO) enzyme in the presence of oxygen to form PPO (2-oxo-4-(hydroxy (methyl) phosphinoyl) butyric acid) in an oxidation step;

aminating the PPO by a transaminase (TA) enzyme, using an amine group from one or more amine donors to form L-glufosinate and an alpha ketoacid by-product in an amination step; and reducing an amount of the alpha ketoacid by-product in a reduction step, wherein more than 90% of the PPO is converted to L-glufosinate, wherein the DAAO enzyme is a mutant DAAO comprising mutations at positions 54, 56, 58, and 213 using SEQ ID NO:8 as a reference sequence, wherein the mutations comprise N54V, T56N, F58H, and M213S, wherein the TA enzyme has the amino acid sequence of SEQ ID NO:7, wherein the alpha ketoacid by-product is reduced in amount by an addition of ketoglutarate decarboxylase (KGD), and wherein the reduction of the amount of the alpha ketoacid by-product allows the amination step to proceed at a higher rate than without such reduction and/or reach an equilibrium concentration that results in a higher yield of L-glufosinate than without such reduction.

2. The method of claim 1, wherein more than 98% of the PPO is converted to L-glufosinate.

3. The method of claim 1, wherein the alpha ketoacid by-product is reduced in amount by enzymatic conversion.

4. The method of claim 1, wherein the TA enzyme is a GabT transaminase.

5. The method of claim 1, wherein the one or more amine donors comprises glutamate or L-glutamate.

6. The method of claim 1, wherein the oxidation, the amination, and the reduction steps are performed in a single container.

7. The method of claim 1, wherein all reagents are added at the start of the reaction.

8. The method of claim 6, wherein reagents for the oxidation, the amination, and the reduction steps are added to the single container at different times.

9. The method of claim 1, wherein the oxidation, the amination, and the reduction steps are performed in separate containers.

10. The method of claim 1, wherein the KGD comprises an amino acid sequence selected from SEQ ID NOS: 1, 2, 3, 4, or 5.

* * * * *